(12) United States Patent
Guyaux et al.

(10) Patent No.: US 7,361,668 B2
(45) Date of Patent: Apr. 22, 2008

(54) QUINUCLIDINE DERIVATIVES PROCESSES FOR PREPARING THEM AND THEIR USES AS M2 AND/OR M3 MUSCARINIC RECEPTOR INHIBITORS

(75) Inventors: Michel Guyaux, Brussels (BE); Chimmanamada U. Dinesh, Waltham, MA (US); Charles Mioskowski, Strasbourg (FR); Luc Quere, Dampicourt (BE); Jean-Philippe Starck, Gougenheim (FR); Patrice Talaga, Watermael-Boitsfort (BE); Alain Wagner, Strasbourg (FR); Matteo Zanda, Gandino (IT)

(73) Assignee: UCB, S.A., Brussels (BE)

( * ) Notice: Subject to any disclaimer, the term of this patent is extended or adjusted under 35 U.S.C. 154(b) by 232 days.

(21) Appl. No.: 10/490,436

(22) PCT Filed: Sep. 23, 2002

(86) PCT No.: PCT/EP02/10644

§ 371 (c)(1),
(2), (4) Date: May 7, 2004

(87) PCT Pub. No.: WO03/033495

PCT Pub. Date: Apr. 24, 2003

(65) Prior Publication Data

US 2005/0020660 A1    Jan. 27, 2005

(30) Foreign Application Priority Data

Oct. 17, 2001 (EP) ................................. 01124727

(51) Int. Cl.
*A61K 31/45* (2006.01)
*A61K 43/96* (2006.01)
*A61K 43/40* (2006.01)
*C07D 453/02* (2006.01)

(52) U.S. Cl. ...................... 514/305; 514/341; 514/406; 546/133; 546/137

(58) Field of Classification Search ................. 546/133, 546/137; 514/406, 305, 341
See application file for complete search history.

(56) References Cited

U.S. PATENT DOCUMENTS 4,644,003 A    2/1987  Rzeszotarski et al.
5,227,394 A *  7/1993  Plate et al. .................. 514/406
5,384,462 A *  1/1995  Levitt .......................... 250/374
5,654,315 A *  8/1997  Brown et al. ................ 514/305
5,691,349 A * 11/1997  Mallion et al. ............. 514/305
5,714,496 A *  2/1998  Brown et al. ................ 514/305
5,770,608 A *  6/1998  Brown et al. ................ 514/305
5,830,902 A * 11/1998  Isaka et al. .................. 514/305

FOREIGN PATENT DOCUMENTS

| EP | 0 812 840 | 12/1997 |
| WO | 93 13096 | 7/1993 |
| WO | 94 03451 | 2/1994 |
| WO | 94 05660 | 3/1994 |
| WO | 94 14085 | 6/1994 |
| WO | 01 23383 | 4/2001 |
| WO | 01 64656 | 9/2001 |
| WO | 02 076973 | 10/2002 |
| WO | WO03/033495 | * 4/2003 |

OTHER PUBLICATIONS

McGraw—Hill Dictionary of Chemical Terms (1990),pp. 282.*
Concise Encyclopedia Chemistry, (1993) pp. 490.*
Hawley's Condensed Chemical Dictionary, 20ed., (1993) pp. 594.*
Patent Abstracts of Japan, vol. 1996, No. 09 (1996) & JP 08 134067 (Yamanouchi Pharmaceutical Co Ltd) (1996); abstract.
Brown, G.R. et al., J. Med. Chem., vol. 42, No. 7, p. 1306-1311 (1999).
Coope J.F. et al., Tetrahedron: Asymmetry, vol. 6, No. 6, p. 1393-1398 (1995).
Sandmann, R.A. et al., Journal of Pharmaceutical Sciences, vol. 66, No. 6, p. 890-891 (1966).
Arnoldi A., et al., Pestic. Sci., vol. 13, p. 670-678 (1982).
Libman, N.M. et al., Pharmaceutical Chemistry Journal, vol. 20, No. 11, p. 759-763 (1986).
Nilsson J.L.G. et al., Acta Pharm. Suecica, vol. 5, p. 9-14 (1968).

* cited by examiner

*Primary Examiner*—Janet L. Andres
*Assistant Examiner*—Raymond Covington
(74) *Attorney, Agent, or Firm*—Wenderoth, Lind & Ponack, L.L.P.

(57) ABSTRACT

The invention concerns quinuclidine derivatives of formula I or II wherein the substituents are as defined in the specification, as well as their use as pharmaceuticals. The compounds of the invention show high affinities for m3 and/or m2 muscarinic receptors and are particularly suited for treating urinary incontinence.

14 Claims, No Drawings

QUINUCLIDINE DERIVATIVES PROCESSES FOR PREPARING THEM AND THEIR USES AS M2 AND/OR M3 MUSCARINIC RECEPTOR INHIBITORS

The present invention concerns quinuclidine derivatives, process for preparing them, pharmaceutical compositions containing them and their use as pharmaceuticals.

Alpha-(1-azabicyclo[2.2.2]oct-3-ylethynyl)-alpha-phenyl benzenemethanol (or 3-(3',3'-diphenyl-3'-hydroxy-1'-propynyl)quinuclidine) is known as possessing marked muscarinic anticholinergic activity (Abstract from N. M. LIBMAN et al., Khim. Farm. Zh. ((1986), 20 (11), 1308-1312).

It has now surprisingly been found that certain analogs of the above mentioned compound demonstrate markedly improved therapeutic properties.

In one aspect, the invention therefore provides a compound having the formula I or II, or a pharmaceutically acceptable salt thereof,

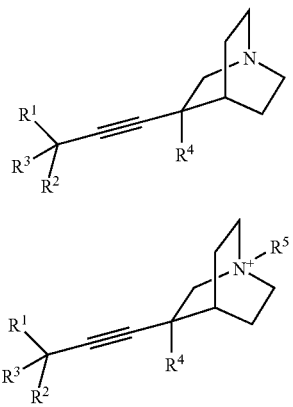

wherein $R^1$ is hydrogen, halogen, alkyl, cyano, hydroxy or an oxy derivative;

$R^2$ is alkyl, alkenyl, alkynyl, aryl, heterocycle or aralkyl;

$R^3$ is alkynyl, aryl, heterocycle or aralkyl;

$R^4$ is hydroxy, halogen or an oxy derivative; and $R^5$ is oxygen, alkyl or aralkyl, with the proviso that $R^2$ and $R^3$ groups can be linked together forming a cycle.

In the definitions set forth below, unless otherwise stated, $R^6$ and $R^7$ are the same or different and each is independently amido, alkyl, alkenyl, alkynyl, ester, ether, aryl, aralkyl, heterocycle or an oxy derivative, thio derivative, acyl derivative, amino derivative, sulfonyl derivative, or sulfinyl derivative, each optionally substituted with any suitable group, including, but not limited to, one or more moieties selected from lower alkyl or other groups as described below as substituents for alkyl.

The term "alkyl", as used herein, is defined as including saturated, monovalent hydrocarbon radicals having straight, branched or cyclic moieties or combinations thereof and containing 1-20 carbon atoms, preferably 1-6 carbon atoms for non-cyclic alkyl and 3-8 carbon atoms for cycloalkyl (in these two preferred cases, unless otherwise specified, "lower alkyl") and includes alkyl moieties optionally substituted by 1 to 5 substituents independently selected from the group consisting of halogen, hydroxy, thiol, amino, nitro, cyano, thiocyanato, acyl derivative, sulfonyl derivative, sulfinyl derivative, alkylamino, carboxy, ester, ether, amido, azido, cycloalkyl, sulfonic acid, sulfonamide, thio derivative, oxyester, oxyamido, heterocycle, vinyl, C1-5-alkoxy, C6-10-aryloxy and C6-10-aryl.

Preferred alkyl groups are methyl, ethyl, propyl, isopropyl, butyl, iso- or ter-butyl, and 2,2-dimethylpropyl each optionally substituted by at least one substituent selected from the group consisting of halogen, hydroxy, thiol, amino, nitro and cyano, such as trifluoromethyl, trichloromethyl, 2,2,2-trichloroethyl, 1,1-dimethyl-2,2-dibromoethyl, 1,1-dimethyl-2,2,2-trichloroethyl.

The term "cycloalkyl", as used herein, refers to a monovalent group of 3 to 20 carbons derived from a saturated cyclic or polycyclic hydrocarbon such as adamantyl, which can optionally be substituted with any suitable group, including but not limited to one or more moieties selected from alkyl or other groups as described above for the alkyl groups. Non-limiting examples are cyclopropyl, cyclobutyl, cyclopentyl, cyclohexyl, cycloheptyl, cyclooctyl, bicyclo[3.2.1]cyclooctyl or adamantyl.

The term "alkenyl" as used herein, is defined as including straight and cyclic, branched and unbranched, unsaturated hydrocarbon radicals having at least one double bond such as ethenyl (=vinyl), 1-methyl-1-ethenyl, 2-methyl-1-propenyl, 1-propenyl, 2-propenyl (=allyl), 1-butenyl, 2-butenyl, 3-butenyl, 4-pentenyl, 1-methyl-4-pentenyl, 3-methyl-1-pentenyl, 1-hexenyl, 2-hexenyl, and the like and being optionally substituted by at least one substituent selected from the group consisting of halogen, hydroxy, thiol, amino, nitro, cyano, aryl and heterocycle such as mono- and di-halo vinyl where halo is fluoro, chloro or bromo.

The term "alkynyl" as used herein, is defined as including straight and cyclic, branched and unbranched, unsaturated hydrocarbon radical containing at least one carbon-carbon triple bond, for example ethynyl, 2-propynyl (=propargyl), and the like and being optionally substituted by at least one substituent selected from the group consisting of halogen, hydroxy, thiol, amino, nitro, cyano, trimethylsilyl, aryl and heterocycle, such as haloethynyl.

When present as bridging groups, alkyl, alkenyl and alkynyl represent straight or branched chains, C1-12-, preferably C1-4-alkylene or C2-12-, preferably C2-4-alkenylene or -alkynylene moieties respectively.

Groups where branched derivatives are conventionally qualified by prefixes such as "n", "sec", "iso" and the like (e.g. "n-propyl", "sec-butyl") are in the n-form unless otherwise stated.

The term "aryl" as used herein, is defined as including an organic radical derived from an aromatic hydrocarbon consisting of 1-3 rings and containing 6-30 carbon atoms by removal of one hydrogen, such as phenyl and naphthyl each optionally substituted by 1 to 5 substituents independently selected from halogen, hydroxy, thiol, amino, nitro, cyano, acyl derivative, sulfonyl, sulfinyl, alkylamino, carboxy, ester, ether, amido, azido, sulfonic acid, sulfonamide, alkylsulfonyl, alkylsulfinyl, alkylthio, oxyester, oxyamido, aryl, C1-6-alkoxy, C6-10-aryloxy, C1-6-alkyl, C1-C6 alkenyl, C1-C6 alkynyl, C1-6-haloalkyl, with the proviso that 2 or more substituents may form a ring attached to the aryl moiety. Preferred aryl groups are phenyl and naphthyl each optionally substituted by 1 to 5 substituents independently selected from halogen, nitro, amino, azido, C1-6-alkoxy, C1-6-alkylthio, C1-6-alkyl, C1-6-haloalkyl and phenyl.

The term "aralkyl", as used herein, represents a group of the formula —$R^8$-aryl in which $R^8$ is C1-12-straight or branched alkylene, or C2-12-straight or branched alkenylene or alkynylene groups. Non-limiting examples are benzyl, halobenzyl, cyanobenzyl, methoxybenzyl, nitrobenzyl, 2-phenylethyl, diphenylmethyl, (4-methoxyphenyl)diphenylmethyl, anthracenylmethyl.

The term "halogen", as used herein, includes an atom of Cl, Br, F, I.

The term "hydroxy", as used herein, represents a group of the formula —OH.

The term "thiol", as used herein, represents a group of the formula —SH.

The term "cyano", as used herein, represents a group of the formula —CN.

The term "nitro", as used herein, represents a group of the formula —NO$_2$.

The term "nitrooxy", as used herein, represents a group of the formula —ONO$_2$.

The term "amino", as used herein, represents a group of the formula —NH$_2$.

The term "azido", as used herein, represents a group of the formula —N$_3$

The term "carboxy", as used herein, represents a group of the formula —COOH.

The term "sulfonic acid", as used herein, represents a group of the formula —SO$_3$H.

The term "sulfonamide", as used herein, represents a group of the formula —SO$_2$NH$_2$.

The term "ester" as used herein is defined as including a group of formula —COO—R$^{6a}$ wherein R$^{6a}$ is such as defined for R$^6$ above except oxy derivative, thio derivative or amino derivative.

The term "oxy derivative", as used herein is defined as including —O—R$^{6b}$ groups wherein R$^{6b}$ is such as defined for R$^6$ above except for "oxy derivative". Non-limiting examples are alkoxy, alkenyloxy, alcynyloxy, acyloxy, esteroxy, amidooxy, alkylsulfonyloxy, alkylsulfinyloxy, arylsulfonyloxy, arylsumflnyloxy, aryloxy, aralkoxy or heterocyclooxy such as pentyloxy, allyloxy, methoxy, ethoxy, phenoxy, benzyloxy, 2-naphthyloxy, 2-pyridyloxy, methylenedioxy, carbonate. Preferred are O—R$^{6b}$ wherein R$^{6b}$ is an alkyl, aryl or aralkyl.

The term "thio derivative", as used herein, is defined as including —S—R$^{6c}$ groups wherein R$^{6c}$ is such as defined for R$^6$ above except for "thio derivative". Non-limiting examples are alkylthio, alkenylthio, alkynylthio and arylthio.

The term "acyl derivative", as used herein, represents a radical derived from carboxylic acid and thus is defined as including groups of the formula R$^{6d}$—CO—, wherein R$^{6d}$ is such as defined for R$^6$ above and may also be hydrogen. Non-limiting examples are formyl, acetyl, propionyl, isobutyryl, valeryl, lauroyl, heptanedioyl, cyclohexanecarbonyl, crotonoyl, fumaroyl, acryloyl, benzoyl, naphthoyl, furoyl, nicotinoyl, 4-carboxybutanoyl, oxalyl, ethoxalyl, cysteinyl, oxamoyl.

The term "amino derivative", as used herein, is defined as including —NHR$^{6e}$ or —NR$^{6e}$R$^{7e}$ groups wherein R$^{6e}$ and R$^{7e}$ are such as defined above for R$^6$ and R$^7$, respectively. Non-limiting examples are mono- or di-alkyl-, alkenyl-, alkynyl- and arylamino or mixed amino.

The term "sulfonyl derivative", as used herein, is defined as including a group of the formula —SO$_2$—R$^{6f}$, wherein R$^{6f}$ is such as defined above for R$^6$ except for "sulfonyl derivative". Non-limiting examples are alkylsulfonyl, alkenylsulfonyl, alkynylsulfonyl and arylsulfonyl.

The term "sulfinyl derivative", as used herein, is defined as including a group of the formula —SO—R$^{6g}$, wherein R$^{6g}$ is such as defined above for R$^6$ except for "sulfinyl derivative". Non-limiting examples are alkylsulfinyl, alkenylsulfinyl, alkynylsulfinyl and arylsulfinyl.

The term "ether" is defined as including a group selected from C1-50-straight or branched alkyl, or C2-50-straight or branched alkenyl or allyl groups or a combination of the same, interrupted by one or more oxygen atoms.

The term "amido" is defined as including a group of formula —CONH$_2$ or —CONHR$^{6h}$ or —CONR$^{6h}$R$^{7h}$ wherein R$^{6h}$ and R$^{7h}$ are such as defined above for R$^6$ and R$^7$, respectively.

The term "heterocycle", as used herein is defined as including an aromatic or non aromatic cyclic alkyl, alkenyl, or allynyl moiety as defined above, having at least one O, S and/or N atom interrupting the carbocyclic ring structure and optionally, one of the carbon of the carbocyclic ring structure may be replaced by a carbonyl. Non-limiting examples of aromatic heterocycles are pyridyl, furyl, pyrrolyl, thienyl, isothiazolyl, imidazolyl, benzimidazolyl, tetrazolyl, quinazolinyl, quinolizinyl, naphthyridinyl, pyridazinyl, pyrimidinyl, pyrazinyl, quinolyl, isoquinolyl, isobenzofuranyl, benzothienyl, pyrazolyl, indolyl, indolizinyl, purinyl, isoindolyl, carbazolyl, thiazolyl, 1,2,4-thiadiazolyl, thieno (2,3-b)furanyl, furopyranyl, benzofuranyl, benzoxepinyl, isooxazolyl, oxazolyl, thianthrenyl, benzothiazolyl, or benzoxazolyl, cinnolinyl, phthalazinyl, quinoxalinyl, phenanthridinyl, acridinyl, perimlidinyl, phenanthrolinyl, phenothiazinyl, furazanyl, isochromanyl, indolinyl, xanthenyl, hypoxanthinyl, pteridinyl, 5-azacytidinyl, 5-azauracilyl, triazolopyridinyl, imidazolopyridinyl, pyrrolopyrimidinyl, and pyrazolopyrimidinyl optionally substituted by alkyl or as described above for the alkyl groups. Non-limiting examples of non aromatic heterocycles are tetrahydrofuranyl, tetrahydropyranyl, piperidinyl, piperidyl, piperazinyl, imidazolidinyl, morpholino, morpholinyl, 1-oxaspiro(4.5) dec-2-yl, pyrrolidinyl, 2-oxo-pyrrolidinyl, 8-thia bicyclo [3.2.1]cyclooctanyl, 1,4-dithiepanyl, tetrahydro-2H-thiopyranyl, or the same which can optionally be substituted with any suitable group, including but not limited to one or more moieties selected from lower alkyl, or other groups as described above for the alkyl groups. The term "heterocycle" also includes bicyclic, tricyclic and tetracyclic, spiro groups in which any of the above heterocyclic rings is fused to one or two rings independently selected from an aryl ring, a cycloalkane ring, a cycloalkene ring or another monocyclic heterocyclic ring or where a monocyclic heterocyclic group is bridged by an alkylene group, such as quinuclidinyl, 7-azabicyclo(2.2.1)heptanyl, 7-oxabicyclo(2.2.1)heptanyl, 8-azabicyclo(3.2.1)octanyl.

Preferably R$^1$ is hydrogen, halogen, hydroxy, cyano, lower alkyl or —O—R$^{6b}$ wherein R$^{6b}$ is an alkyl group, an acyl derivative or an alkyl group substituted with an ester, most preferably R$^1$ is hydrogen, fluor, methyl, cyano, hydroxy, methoxy, —OC(=O)CH$_3$ or —OCH$_2$COOCH$_3$.

Preferably R$^2$ is an alkyl, alkenyl, aryl, heterocycle or aralkyl. More preferably R$^2$ is an alkyl, cycloalkyl, alkenyl or cycloalkenyl comprising from 3 to 15 carbon atoms; phenyl optionally substitued by an halogen, an alkyl or a halogen-substituted alkyl such as trifluoromethyl; heterocycle optionally substitued by an halogen; or benzyl.

Preferably R$^3$ is alkynyl, aryl, heterocycle or benzyl. More preferably R$^3$ is alkynyl comprising from 2 to 5 carbon atoms; naphtyl; phenyl; phenyl substituted with an halogen, an alkyl, an halogen-substituted alkyl, alkoxy, amino derivative, carboxy, an ester, aryloxy; an heterocycle; an heterocycle substitued with an halogen or a nitro; or benzyl.

When R$^2$ and R$^3$ groups are linked together so that they form a cycle, R$^2$ and R$^3$ are preferably phenyl groups. Particularly preferred are 5H-dibenzo-[a,d]cycloheptenyl and 10,11-dihydro-5H-dibenzo-[a,d]cycloheptenyl.

Preferably R$^4$ is hydroxy, halogen or —O—R$^{6b}$ wherein R$^{6b}$ is an alkyl or aralkyl, most preferably hydroxy, fluoro, methoxy, ethoxy, benzyloxy or (3-methylbenzyl)oxy.

Preferably R$^5$ is oxygen, alkyl or aralkyl, most preferably oxygen, methyl or benzyl.

Combinations of one or more of these preferred compound groups are especially preferred.

Preferred compounds according to the invention are compounds of formula I or II, wherein R$^1$ is hydrogen, fluor, methyl, cyano, hydroxy, —OCH$_3$ or —OCH$_2$COOCH$_3$;

R$^2$ is alkyl, alkenyl, aryl, heterocycle or benzyl;

R$^3$ is alkynyl, aryl, heterocycle or benzyl;

R$^4$ is hydroxy, fluoro, —OCH$_3$, —OCH$_2$CH$_3$ or —Obenzyl; and

R$^5$ is oxygen, methyl or benzyl.

Particularly preferably R$^1$ is hydroxy, cyano or fluor.

Particularly preferably R$^2$ is n-butyl, n-pentyl, iso-pentyl, neopentyl, cyclopentyl, cyclopentylmethyl, 1-buten-3-yl, cyclohexyl, cycloheptyl, cyclooctyl, cycloheptenyl, cyclobutyl, phenyl, benzyl, 5-pyrimidinyl, 3-pyridinyl, 4-pyridinyl, 3-fluorophenyl, 4-fluorophenyl, 4-chlorophenyl, 3-thienyl, 2-thienyl, 5-chloro-2-thienyl, 1-adamantyl, 1-bicyclo(2.2.1)hept-5-en-2-yl, 1,4-dithiepan-6-yl, thiomorpholino-4-yl, 1-bicyclo(3.2.1)oct-3-yl or 8-thiabicyclo (3.2.1)oct-3-yl,.

Particularly preferably R$^3$ is ethynyl, phenyl, 5-pyrimidinyl, benzyl, 4-methylphenyl, 4-fluorophenyl, 4-chlorophenyl, 3-fluorophenyl, 3-methylphenyl, cycloheptyl, 2-pyridinyl, 3-pyridinyl, 2-fluoro-3-pyridinyl, 6-fluoro-3-pyridinyl, 3-pyridinyl, 2,3-dihydro-1H-inden-5-yl, 2-thienyl or 3-thienyl.

Particularly preferably R$^4$ is fluoro or —OCH$_3$.

Particularly preferably R$^5$ is —CH$_3$.

Combinations of one or more of these preferred compound groups are especially preferred.

The compounds of formula I or II have at least one stereogenic center in their structure, i.e. the carbon atom of the quinuclidine cycle to which R$^4$ is attached. This stereogenic center may be present in a R or a S configuration, said R and S notation is used in correspondance with the rules described in Pure Appl. Chem., 45 (1976) 11-30.

In all the above mentioned scopes the carbon atom to which R$^4$ is attached is preferably in the "R" configuration.

Depending on the nature of the substituents R$^1$, R$^2$ and R$^3$, the carbon atom to which these substituents are attached can also be a stereogenic center. This stereogenic center may be present in a R or a S configuration. Preferably this second stereogenic center is in the "R" configuration.

The invention also relates to all stereoisomeric forms such as enantiomeric and diastereoisomeric forms of the compounds of formula I or II or mixtures thereof (including all possible mixtures of stereoisomers).

Furthermore certain compounds of formula I or II which contain alkenyl groups may exist as Z (zusammen) or E (entgegen) isomers. In each instance, the invention includes both mixture and separate individual isomers.

With respect to the present invention reference to a compound or compounds is intended to encompass that compound in each of its possible isomeric forms and mixtures thereof unless the particular isomeric form is referred to specifically.

Most preferred compounds are:

3-(3-methoxy-1-azabicyclo[2.2.2]oct-3-yl)-1,1-diphenyl-2-propyn-1-ol;

3-[(3R)-3-methoxy-1-azabicyclo[2.2.2]oct-3-yl]-1,1-diphenyl-2-propyn-1-ol;

4-(3-methoxy-1-azabicyclo[2.2.2]oct-3-yl)-2,2-diphenyl-3-butynenitrile;

3-[(3R)-3-methoxy-1-azabicyclo[2.2.2]oct-3-yl]-1-(3-methylphenyl)-1-phenylprop-2-yn-1-ol;

1-(2-fluoro-3-pyridinyl)-3-[(3R)-3-methoxy-1-azabicyclo[2.2.2]oct-3-yl]-1-phenyl-2-propyn-1-ol;

1-(2,3-dihydro-1H-inden-5-yl)-3-[(3R)-3-methoxy-1-azabicyclo[2.2.2]oct-3-yl]-1-phenyl-2-propyn-1-ol;

1-(3-methoxy-1-azabicyclo[2.2.2]oct-3-yl)-3-phenyl-1-heptyn-3-ol;

1-[(3R)-3-methoxy-1-azabicyclo[2.2.2]oct-3-yl]-3-phenyl-1-heptyn-3-ol;

1-cyclopentyl-3-[(3R)-3-methoxy-1-azabicyclo[2.2.2]oct-3-yl]-1-phenyl-2-propyn-1-ol;

1-cyclooctyl-3-[(3R)-3-methoxy-1-azabicyclo[2.2.2]oct-3-yl]-1-phenyl-2-propyn-1-ol;

1-cyclohexyl-3-(3-methoxy-1-azabicyclo[2.2.2]oct-3-yl)-1-phenyl-2-propyn-1-ol;

(1R)-1-cyclohexyl-3-[(3R)-3-methoxy-1-azabicyclo[2.2.2]oct-3-yl]-1-phenyl-2-propyn-1-ol;

(1S)-1-cyclohexyl-3-[(3R)-3-methoxy-1-azabicyclo[2.2.2]oct-3-yl]-1-phenyl-2-propyn-1-ol;

1-cyclohexyl-3-(3-fluoro-1-azabicyclo[2.2.2]oct-3-yl)-1-phenylprop-2-yn-1-ol;

(3R)-3-(3-cyclohexyl-3-fluoro-3-phenyl-1-propynyl)-3-methoxy-1-azabicyclo[2.2.2]octane;

1-cyclohexyl-3-[(3R)-3-methoxy-1-azabicyclo[2.2.2]oct-3-yl]-1-(2-thienyl)-2-propyn-1-ol;

1-cycloheptyl-3-[(3R)-3-methoxy-1-azabicyclo[2.2.2]oct-3-yl]-1-phenyl-2-propyn-1-ol;

(1R)-1-cycloheptyl-3-[(3R)-3-methoxy-1-azabicyclo[2.2.2]oct-3-yl]-1-propyn-1-ol;

(1S)-1-cycloheptyl-3-[(3R)-3-methoxy-1-azabicyclo[2.2.2]oct-3-yl]-1-phenyl-2-propyn-1-ol;

(3R)-3-[(3R)-3-cycloheptyl-3-hydroxy-3-phenyl-1-propynyl]-3-methoxy-1-methyl-1-azoniabicyclo[2.2.2]octane iodide;

1-cycloheptyl-3-[(3R)-3-methoxy-1-azabicyclo[2.2.2]oct-3-yl]-1-(3-pyridinyl)-2-propyn-1-ol;

1-cycloheptyl-1-(2-fluoro-3-pyridinyl)-3-[(3R)-3-methoxy-1-azabicyclo[2.2.2]oct-3-yl]-2-propyn-1-ol;

1-(4-cyclohepten-1-yl)-3-[(3R)-3-methoxy-1-azabicyclo[2.2.2]oct-3-yl]-1-phenyl-2-propyn-1-ol;

1-cyclobutyl-3-[(3R)-3-methoxy-1-azabicyclo[2.2.2]oct-3-yl]-1-phenyl-2-propyn-1-ol;

3-[(3R)-3-methoxy-1-azabicyclo[2.2.2]oct-3-yl]-1-phenyl-1-(5-pyrimidinyl)-2-propyn-1-ol;

3-[(3R)-3-methoxy-1-azabicyclo[2.2.2]oct-3-yl]-1-phenyl-1-(4-pyridinyl)-2-propyn-1-ol;

1-(4-fluorophenyl)-1-(6-fluoro-3-pyridinyl)-3-[(3R)-3-methoxy-1-azabicyclo[2.2.2]oct-3-yl]-2-propyn-1-ol;

1,1-bis(4-fluorophenyl)-3-(3-methoxy-1-azabicyclo[2.2.2]oct-3-yl)-2-propyn-1-ol;

1-(4-fluorophenyl)-1-(2-fluoro-3-pyridinyl)-3-[(3R)-3-methoxy-1-azabicyclo[2.2.2]oct-3-yl]-2-propyn-1-ol;

1,1-bis(4-chlorophenyl)-3-(3-methoxy-1-azabicyclo[2.2.2]oct-3-yl)-2-propyn-1-ol;

3-[(3R)-3-methoxy-1-azabicyclo[2.2.2]oct-3-yl]-1,1-di(3-thienyl)-2-propyn-1-ol;

3-[(3R)-3-methoxy-1-azabicyclo[2.2.2]oct-3-yl]-1-phenyl-1-(3-pyridinyl)-2-propyn-1-ol;

(1R)-3-[(3R)-3-methoxy-1-azabicyclo[2.2.2]oct-3-yl]-1-phenyl-1-(3-pyridinyl)-2-propyn-1-ol;

1,1-bis(3-fluorophenyl)-3-[(3R)-3-methoxy-1-azabicyclo[2.2.2]oct-3-yl]-2-propyn-1-ol;

3-(3-methoxy-1-azabicyclo[2.2.2]oct-3-yl)-1,1-dithien-2-ylprop-2-yn-1-ol;

3-[(3R)-3-methoxy-1-azabicyclo[2.2.2]oct-3-yl]-1,1-di(2-thienyl)-2-propyn-1-ol;
(3R)-3-[3-hydroxy-3,3-di(2-thienyl)-1-propynyl]-3-methoxy-1-methyl-1-azoniabicyclo[2.2.2]octane iodide;
1-(1-adamantyl)-3-[(3R)-3-methoxy-1-azabicyclo[2.2.2]oct-3-yl]-1-phenyl-2-propyn-1-ol;
1-bicyclo[2.2.1]hept-5-en-2-yl-3-(3-methoxy-1-azabicyclo[2.2.2]oct-3-yl)-1-phenyl-2-propyn-1-ol;
4-ethyl-1-[(3R)-3-methoxy-1-azabicyclo[2.2.2]oct-3-yl]-3-phenyl-1-hexyn-3-ol;
1-[(3R)-3-methoxy-1-azabicyclo[2.2.2]oct-3-yl]-3-phenyl-6-hepten-1-yn-3-ol;
1-(1,4-dithiepan-6-yl)-3-[(3R)-3-methoxy-1-azabicyclo[2.2.2]oct-3-yl]-1-phenyl-2-propyn-1-ol;
3-[(3R)-3-methoxy-1-azabicyclo[2.2.2]oct-3-yl]-1-phenyl-1-tetrahydro-2H-thiopyran-4-yl-2-propyn-1-ol;
1-bicyclo[3.2.1]oct-3-yl-3-[(3R)-3-methoxy-1-azabicyclo[2.2.2]oct-3-yl]-1-phenyl-2-propyn-1-ol;
3-[(3R)-3-methoxy-1-azabicyclo[2.2.2]oct-3-yl-1-phenyl-1-(8-thiabicyclo[3.2.1]oct-3-yl)-2-propyn-1-ol;
1-[(3R)-3-methoxy-1-azabicyclo[2.2.2]oct-3-yl]-3-phenyl-1-octyn-3-ol;
1-[(3R)-3-methoxy-1-azabicyclo[2.2.2]oct-3-yl]-5,5-dimethyl-3-(2-thienyl)-1-hexyn-3-ol;
1-cyclopentyl-4-[(3R)-3-methoxy-1-azabicyclo[2.2.2]oct-3-yl]-2-(2-thienyl)-3-butyn-2-ol;
1-(5-chloro-2-thienyl)-3-[(3R)-3-methoxy-1-azabicyclo[2.2.2]oct-3-yl]-1-(2-pyridinyl)-2-propyn-1-ol.

The "pharmaceutically acceptable salts" according to the invention include therapeutically active, non-toxic base and acid salt forms which the compounds of formula I or II are able to form.

The acid addition salt form of a compound of formula I or II that occurs in its free form as a base can be obtained by treating the free base with an appropriate acid such as an inorganic acid, for example, a hydrohalic such as hydrochloric or hydrobromic, sulfuric, nitric, phosphoric and the like; or an organic acid, such as, for example, acetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like.

The compounds of formula I or II containing acidic protons may be converted into their therapeutically active, non-toxic base addition salt forms, e.g. metal or amine salts, by treatment with appropriate organic and inorganic bases. Appropriate base salt forms include, for example, ammonium salts, alkali and earth alkaline metal salts, e.g. lithium, sodium, potassium, magnesium, calcium salts and the like, salts with organic bases, e.g. N-methyl-D-glucamine, hydrabamine salts, and salts with amino acids such as, for example, arginine, lysine and the like.

Conversely said salt forms can be converted into the free forms by treatment with an appropriate base or acid.

Compounds of the formula I or II and their salts can be in the form of a solvate, which is included within the scope of the present invention. Such solvates include for example hydrates, alcoholates and the like.

The invention also includes within its scope prodrug forms of the compounds of formula I or II, and its various sub-scopes and sub-groups.

The term "prodrug" as used herein includes compound forms which are rapidly transformed in vivo to the parent compound according to the invention, for example, by hydrolysis in blood. Prodrugs are compounds bearing groups which are modified by biotransformation prior to exhibiting their pharmacological action. Such groups include moieties which are readily oxidised, cyclised or cleaved, which compound after biotransformation remains or becomes pharmacologically active. For example, metabolically cleavable groups form a class of groups well known to practitioners of the art. They include, but are not limited to such groups as alkanoyl (i.e. acetyl, propionyl, butyryl, and the like), unsubstituted and substituted carbocyclic aroyl (such as benzoyl, substituted benzoyl and 1- and 2-naphthoyl), alkoxycarbonyl (such as ethoxycarbonyl), trialkylsilyl (such as trimethyl- and triethylsilyl), monoesters formed with dicarboxylic acids (such as succinyl), phosphate, sulfate, sulfonate, sulfonyl, sulfinyl and the like. The compounds bearing the biotransformable groups have the advantage that they may exhibit improved bioavailability as a result of enhanced solubility and/or rate of absorption conferred upon the parent compound by virtue of the presence of the biotransformable group. T. Higuchi and V. Stella, "Pro-drugs as Novel Delivery System", Vol. 14 of the A.C.S. Symposium Series; "Bioreversible Carriers in Drug Design", ed. Edward B. Roche, American Pharmaceutical Association and Pergamon Press, 1987.

The present invention concerns also processes for preparing the compounds of formula I or II.

The compounds of formula I or II according to their invention can be prepared analogously to conventional methods as understood by the person skilled in the art of synthetic organic chemistry.

The following process description sets forth certain synthesis routes in an illustrative manner. Other alternative and/or analogous methods will be readily apparent to those skilled in this art. As used herein in connection with substituent meanings, "=" means "is" and "≠" means "is other than".

According to one embodiment, compounds having the general formula I wherein $R^1$ is hydroxy may be prepared by reaction of a compound of formula III with a ketone of formula IV according to the equation:

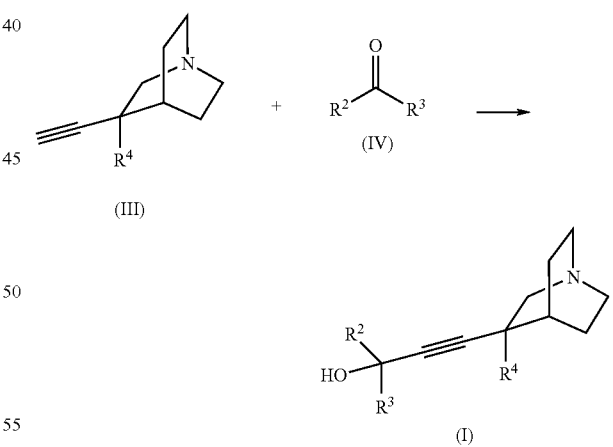

This reaction may be carried out in an inert solvent, for example tetrahydrofurane, between −40° C. and room temperature, in the presence of a strong base such as butyllithium or ethyl magnesium bromide as described in: Unterhalt B., Middelberg C., Arch. Pharm. (1994), 327 (2), 119-120 or in: Hennion G. F., Boisselle A. P., J. Org. Chem. (1961), 26, 2677-2681.

Compounds of formula IV are commercially available or may be prepared under any conventional method known to the person skilled in the art.

Compounds of formula III may be prepared by one of the following processes.

Compounds of formula III wherein $R^4$=OH may be prepared according to the procedure described in Patent Application WO9425459-A1 or in Coope J. F., Main B. G., Tetrahedron Asymmetry (1995), 6 (6), 1393-1398.

For separation purposes, a racemate (or mixture of enantiomers in any proportions) of formula III wherein $R^4$=OH may be transformed into the corresponding acetate according to any conventional procedure known to the person skilled in the art. The resolution of this racemate (or mixture of enantiomers in any proportions) into enantiomers, using most preferably chromatographic separation on chiral phase in reversed or preferably in direct mode, followed by a step of deprotection, leads to enantiomers of formula III wherein $R^4$=OH.

Compounds of formula III wherein $R^4$=—$OR^{6b}$, $R^{6b}$ being an alkyl group, an aryl group or a aralkyl group may be obtained by transformation of the corresponding compound of formula III wherein $R^4$=OH, according to the equation:

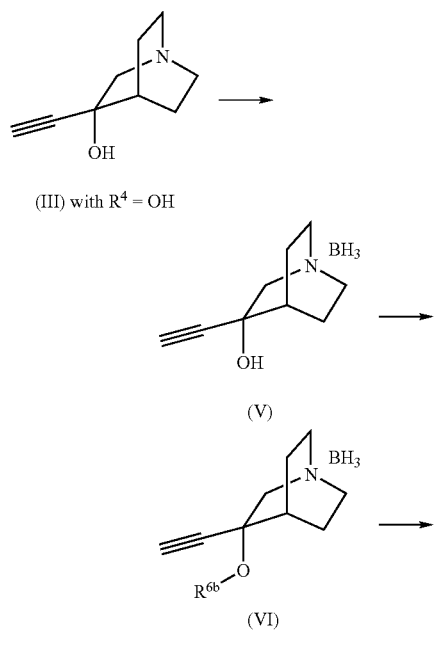

Compounds of formula V may be prepared according to the procedure described in Stotter P. L., Friedman M. D., Dorsey G. O., Shiely R. W., Williams R. F., Minter D. E., Heterocycles (1987), 25, 251-258.

Compounds of formula VI may be prepared by alkylation of compounds of formula V under any conventional method known to the person skilled in the art.

Compounds of formula III wherein $R^4$=$OR^{6b}$ may be obtained by decomplexation of compounds of formula VI in presence of an acid (trifluoroacetic acid or HCl 5M) in a mixture of acetone/ether, between 0° C. and room temperature.

Compounds of formula III wherein $R^4$=halogen may be prepared by halogenation of the corresponding compound of formula III wherein $R^4$=OH, for example with DAST when $R^4$=F. This reaction may be carried out in an inert solvent, for example dichloromethane, between −70° C. and room temperature.

According to another embodiment, compounds having the general formula I, wherein $R^1$ represents alkyl, cyano or oxy derivative and $R^4$=$OR^{6b}$, $R^{6b}$ being an alkyl group, an aryl or an aralkyl group, may be prepared by deprotection of a borane complex of formula VII according to the equation:

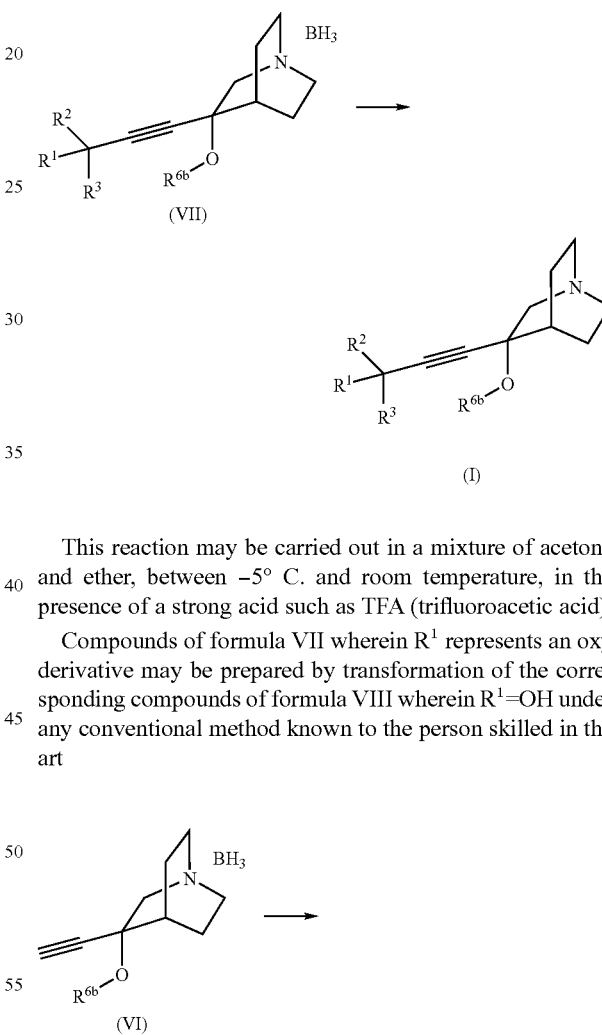

This reaction may be carried out in a mixture of acetone and ether, between −5° C. and room temperature, in the presence of a strong acid such as TFA (trifluoroacetic acid).

Compounds of formula VII wherein $R^1$ represents an oxy derivative may be prepared by transformation of the corresponding compounds of formula VIII wherein $R^1$=OH under any conventional method known to the person skilled in the art

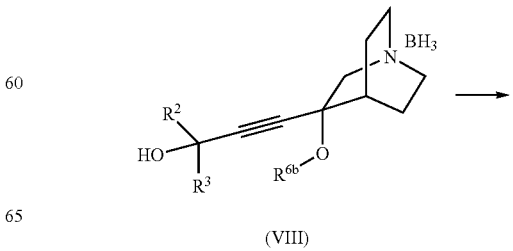

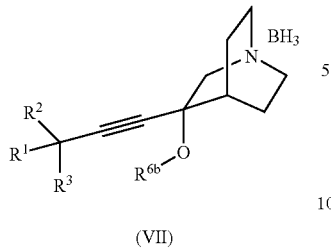

(VII)

Compounds of formula VIII may be prepared by reaction of a compound of formula VI with a ketone of formula IV as already described in A.

According to another embodiment, compounds having the general formula (1), wherein $R^1$ represents hydroxy and $R^4$ represents an oxy derivative, are key synthesis intermediates for corresponding compounds wherein $R^1$ represents halogen.

This halogenation may be carried out for example DAST when $R^1$=F, in an inert solvent, for example dichloromethane, between −70° C. and room temperature and under an inert atmosphere.

According to another embodiment, compounds having the general formula (I), wherein $R^1$ represents hydroxy and $R^4$ represents an oxy derivative, are key synthesis intermediates for corresponding compounds wherein $R^1$ represents hydrogen.

This transformation may be carried according to the procedure described in Batt D. G., Maynard G. D., Petraitis J. J., Shaw J. E., Galbraith W., Harris R. R., J. Med. Chem. (1990), 33, 360-370.

According to another embodiment, compounds having the general formula (I), wherein $R^2$ or $R^3$ represents (trimethylsilyl)ethynyl, are key synthesis intermediates for corresponding compounds wherein $R^2$ or $R^3$ represents ethynyl.

This transformation may be carried according to any procedure known to the person skilled in the art.

According to another embodiment, compounds having the general formula (I), wherein $R^2$ or $R^3$ represents 1-(tert-butoxycarbonyl)-4-piperidinyl, are key synthesis intermediates for corresponding compounds wherein $R^2$ or $R^3$ represents 4-piperidinyl.

This transformation may be carried according to any procedure known to the person skilled in the art.

According to another embodiment, compounds having the general formula I wherein $R^1$ is $CH_3$ or CN and $R^4$=OH may be prepared by reaction of a compound of formula IX with quinuclidinone according to the equation:

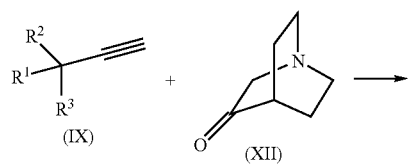

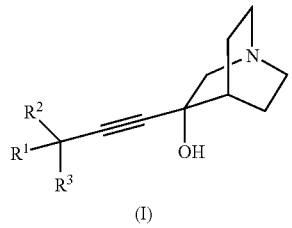

(I)

This reaction may be carried out according to the procedure described in Grangier G., Trigg W. J., Lewis T., Rowan M. G., Potter B. V. L., Blagbrough I. S., Tetrahedron Lett. (1998), 39 (8), 889-892.

Compounds of formula IX may be prepared by one of the following processes.

Compounds of formula IX wherein $R^1$=$CH_3$ may be prepared according to the procedure described in Dehmlow E., Tetrahedron Lett. (1971), 563-566.

Compounds of formula IX wherein R=CN may be prepared according to the equation:

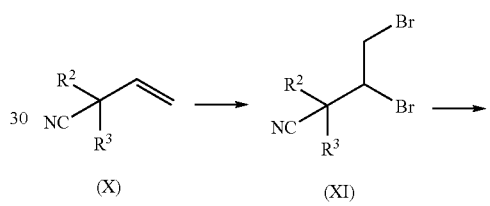

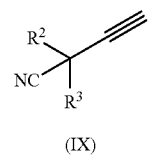

(IX)

Compounds of formula XI may be prepared according to the procedure described in Arumugam S., Verkade J. G., J. Org. Chem. (1997), 62 (14), 4827-4828 Compounds of formula IX may be prepared by reaction of (XI) with tBuOK in anhydrous THF under an inert atmosphere at low temperature.

According to another embodiment, compounds having the general formula (II), wherein $R^5$=O, may be prepared by oxidation of the corresponding compound of formula I. This reaction may be carried out by reaction in ethanol at room temperature, using hydrogen peroxide as oxidant, and a catalytic amount of methyl trioxorhenium.

According to another embodiment, compounds having the general formula (II), wherein $R^5$ represents alkyl or aralkyl, may be prepared by alkylation of the corresponding compound of formula I. This reaction may be carried out according to any procedure known to the person skilled in the art.

In the preparation processes according to the invention, the reaction products may be isolated from the reaction medium and, if necessary, further purified according to methodologies generally known in the art such as, for example extraction, crystallization, distillation, trituration and chromatography, or any combination of the same.

When compounds of formula I or II present one or several stereogenic centres, and that non-stereoselective methods of synthesis are used, resolution of the mixture of stereoisomers can best be effected in one or several steps, involving generally sequential separation of mixtures of diastereomers into their constituting racemates, using preferably chromatographic separations on achiral or chiral phase in reversed or preferably in direct mode, followed by at least one ultimate step of resolution of each racemate into its enantiomers, using most preferably chromatographic separation on chiral phase in reversed or preferably in direct mode. Alternatively, when partly stereoselective methods of synthesis are used, the ultimate step may be a separation of diastereomers using preferably chromatographic separations on achiral or chiral phase in reversed or preferably in direct mode.

In particular, the present invention also concerns the synthesis intermediates prepared during the above described processes.

In another embodiment, the present invention concerns also the synthesis intermediates of formula IIIbis, Vbis, V, VI, VIIbis, VII, VII, IX, X, XI.

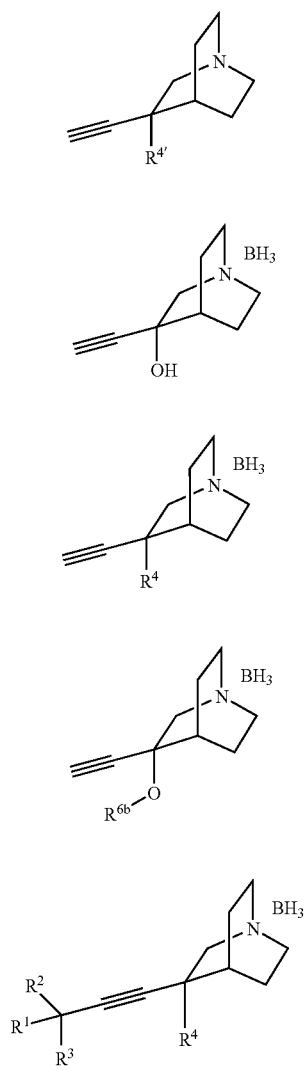

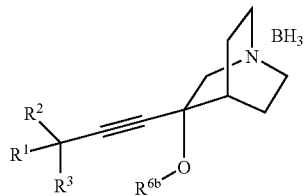

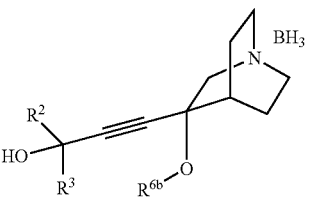

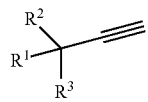

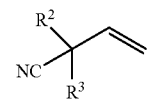

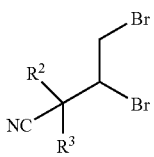

wherein

R$^1$ is hydrogen, halogen; akyl, cyano, hydroxy or an oxy derivative;

R$^2$ is alkyl, alkenyl, alkynyl, aryl, heterocycle or aralkyl;

R$^3$ is alkynyl, aryl, heterocycle or aralkyl;

R$^4$ is hydroxy, halogen or an oxy derivative;

R$^{4'}$ is halogen or an oxy derivative;

R$^5$ is oxygen, alkyl or aralkyl; and

R$^{6b}$ is alkyl or aralkyl, with the proviso that R$^2$ and R$^3$ groups can be linked together forming a cycle.

The present invention concerns preferably the synthesis intermediates having the formula IIIbis wherein R$^{4'}$ is OR$^{6b}$, R$^{6b}$ being an alkyl group or an aralkyl group.

The present invention concerns preferably the synthesis intermediates having the formula VIIbis wherein R$^1$ is alkyl, cyano or oxy derivative and R$^4$ is OR$^{6b}$, R$^{6b}$ being an alkyl group or an aralkyl group.

The present invention concerns preferably the synthesis intermediates having the formula VII wherein R$^{6b}$ represents an alkyl group.

The present invention concerns preferably the synthesis intermediates having the formula IX wherein R$^1$ is CH$_3$.

Preferably, the synthesis intermediates are selected from the group consisting on [1-(methylsulfonyl)-4-piperidinyl] (phenyl)methanone, cyclobutyl(2-pyridinyl)methanone, (5-chloro-2-thienyl) (2-pyridinyl)methanone, 3,3-dimethyl-1-(2-thienyl)-1-butanone, 3,5,5-trimethyl-1-(2-thienyl)-1-hexanone, cycloheptyl(2-thienyl)methanone, 2-cyclopentyl-1-(2-thienyl)ethanone, phenyl(tetrahydro-2H-thiopyran-4- yl)methanone, cycloheptyl(3-pyridinyl)methanone, 4-cyclohepten-1-yl(phenyl)methanone, phenyl(8-thiabicyclo[3.2.1]oct-3-yl)methanone, 1-cycloheptyl-2-butyn-1-one, (2,2-dimethyl-1,3-dioxan-5-yl)(phenyl)methanone, tert-butyl 4-benzoyl-1-piperidinecarboxylate, 1-cycloheptyl-3-(trimethylsilyl)-2-propyn-1-one, cycloheptyl(1-methyl-1H-pyrrol-2-yl)methanone, phenyl[4-(3-phenylpropoxy)phenyl]methanone, (4-fluorophenyl)(2-fluoro-3-pyridinyl)methanone, (4-fluorophenyl)(6-fluoro-3-pyridinyl)methanone, (6-fluoro-3-pyridinyl)(phenyl) methanone, cycloheptyl(2-fluoro-3-pyridinyl)methanone, cycloheptyl(5-pyrimidinyl)methanone, 3,4-dibromo-2,2-diphenylbutanenitrile, 2,2-diphenyl-3-butynenitrile, 3-ethynyl-1-azabicyclo[2.2.2]oct-3-yl acetate, (3R)-3-ethynyl-1-azabicyclo[2.2.2]oct-3-yl acetate, (3R)-3-ethynyl-1-azabicyclo[2.2.2]octan-3-ol compound complexed with borane (1:1), (3R)-3-ethynyl-3-methoxy-1-azabicyclo [2.2.2]octane with borane, (3R)-3-ethynyl-1-azabicyclo [2.2.2]oct-3-yl methyl ether, (3R)-3-ethoxy-3-ethynyl-1-azabicyclo[2.2.2]octane, (3R)-3-(benzyloxy)-3-ethynyl-1-azabicyclo[2.2.2]octane, (3R)-3-ethynyl-3-[(3-methylbenzyl)oxy]-1-azabicyclo[2.2.2]octane, 3-ethynyl-3-fluoroquinuclidine, 3-[(3R)-3-methoxy-1-azabicyclo[2.2.2] oct-3-yl]-1-phenyl-1-(3-pyridinyl)-2-propynyl acetate, 3-[(3R)-3-methoxy-1-azabicyclo[2.2.2]oct-3-yl]-1,1thienyl)-2-propyn-1-ol compound complexed with borane (1:1), methyl {[3-[(3R)-3-methoxy-1-azabicyclo[2.2.2]oct-3-yl]-1,1-di(2-thienyl)-2-propynyl]oxy}acetate compound complexed with borane (1:1), 3-(3,3-diphenyl-1-butynyl)quinuclidin-3-ol, 3-(3,3-diphenyl-1-butynyl)quinuclidin-3-ol complexed with borane (1:1), 3-(3,3-diphenyl-1-butynyl)-1-azabicyclo[2.2.2]oct-3-yl methyl ether compound complexed with borane (1:1), 4-(3-hydroxy-1-azabicyclo[2.2.2] oct-3-yl)-2,2-diphenyl-3-butynenitrile, 4-(3-hydroxy-1-azabicyclo[2.2.2]oct-3-yl)-2,2-diphenyl-3-butynenitrile complexed with borane (1:1), 4-(3-methoxy-1-azabicyclo [2.2.2]oct-3-yl)-2,2-diphenyl-3-butynenitrile compound complexed with borane (1:1), 3-[(3R)-3-methoxy-1-azabicyclo[2.2.2]oct-3-yl]-1,1-diphenyl-2-propyn-1-ol compound complexed with borane (1:1), (3R)-3-methoxy-3-(3-methoxy-3,3-diphenyl-1-propynyl)-1-azabicyclo[2.2.2] octane compound complexed with borane (1:1) and 3-cycloheptyl-1-[(3R)-3-methoxy-1-azabicyclo[2.2.2]oct-3-yl]-5-(trimethylsilyl)-1,4-pentadiyn-3-ol.

It has now been found that compounds of formula I or II and their pharmaceutically acceptable salts are useful in a variety of pharmaceutical indications.

In particular, the present invention concerns the therapeutic use of a compound of formula I or II or a pharmaceutically acceptable salt thereof.

The compounds according to the invention have high affinity for the human m3 muscarinic receptors (up to 0.1 nM). The compounds did not recognize non-muscarinic receptors (55 tested) at 1 µM indicating they are highly selective ligands of muscarinic receptors. These compounds also recognize the m1, m2, m4 and m5 receptors with variable receptor subtype selectivity.

Preferred compounds have been proven to antagonize carbachol induced contraction of guinea-pig bladder in vitro with the most active being at least 10 fold more potent muscarinic antagonist than Oxybutynin and Tolterodine which are drugs curently used for the treatment of urinary incontinence. Most effective antagonists have been proven to be also potent bladder anticontractile agents in vivo based on cystometry performed in the rat and/or guinea pig where they are 10 fold more potent than the clinical references.

The compounds according to the invention may be useful for the treatment of symptoms in connection to lower urinary tract disorders but also to disorders of lower and upper airways, of gastrointestinal tractus, to dysfunction of the cardiac rhythm and to CNS (central nervous system) related disorders causing malfunction of cognition, locomotion, feeding or sleeping.

The compounds according to the invention may be used in the treatment of bladder disorders including urge and mixed urinary incontinence, pollakiuria, neurogenic or unstable bladder, overactive bladder, hypereflexia and cystitis.

The compounds according to the invention may be used in the treatment of diseases associated to airway narrowing or/and mucus hypersecretion such as asthma, chronic bronchitis, rhinitis, coughing and especially chronic obstructive pulmonary disease.

The compounds according to the invention may be used in the treatment of gastrointestinal disorders associated with intestinal hypermotility such as irritable bowel syndrome, spastic colitis, diverticulitis and peptic ulcers.

The compounds according to the invention may be used in the treatment of cognitive disorders causally related to a deterioration or deficit of cortical cholinergic neurones, such as in senile dementia and Alzheimer's disease.

The compounds according to the invention may be used in the treatment of Parkinsonian's disorders and dyskinisia thought to be causely related to a deterioration of dopaminergic neurones in the nigrostriatum.

The compounds according to the invention may be used-in the treatment of obesity, bulimia, metabolic syndrome.

The compounds according to the invention may be usefull for treating sleeping disorders.

The compounds according to the invention may be used in the emergency treatment of acute myocardial infarction where the dominant autonomic influence of the heart is via the vagus nerve, causing sinus or nodal bradycardia.

The present invention concerns the use of a compound of formula I or II or a pharmaceutically acceptable salt thereof, for the manufacture of a medicament.

The present invention also concerns a method for treating symptoms in connection to lower urinary tract disorders but also to disorders of lower and upper airways, of gastrointestinal tractus, to dysfunction of the cardiac rhythm and to CNS (central nervous system) related disorders causing malfunction of cognition, locomotion, feeding or sleeping, in a mammal in need of such treatment, comprising administering a therapeutic dose of at least one compound of formula I or II or a pharmaceutically acceptable salt thereof to a patient.

The methods of the invention comprise administration to a mammal (preferably human) suffering from above mentioned conditions or disorders, of a compound according to the invention in an amount sufficient to alleviate or prevent the disorder or condition.

The compound is conveniently administered in any suitable unit dosage form, including but not limited to one containing 0.01 mg to 1000 mg, preferably 0.1 to 100 mg of active ingredient per unit dosage form.

The term "treatment" as used herein includes curative treatment and prophylactic treatment.

By "curative" is meant efficacy in treating a current symptomatic episode of a disorder or condition.

By "prophylactic" is meant prevention of the occurrence or recurrence of a disorder or condition.

Activity in any of the above mentioned indications can of course be determined by carrying out suitable clinical trials in a manner known to a person skilled in the relevant art for the particular indication and/or in the design of clinical trials in general.

For treating diseases, compounds of formula I or II or their pharmaceutically acceptable salts, may be employed at an effective daily dosage and administered in the form of a pharmaceutical composition.

Therefore, another embodiment of the present invention concerns a pharmaceutical composition comprising an effective amount of a compound of formula I or II or a pharmaceutically acceptable salt thereof in combination with a pharmaceutically acceptable diluent or carrier.

To prepare a pharmaceutical composition according to the invention, one or more of the compounds of formula I or II or a pharmaceutically acceptable salt thereof, is intimately admixed with a pharmaceutical diluent or carrier according to conventional pharmaceutical compounding techniques known to the skilled practitioner.

Suitable diluents and carriers may take a wide variety of forms depending on the desired route of administration, e.g., oral, rectal, or parenteral.

Pharmaceutical compositions comprising compounds according to the invention can, for example, be administered orally or parenterally, i.e., intravenously, intramuscularly or subcutaneously, intrathecally, vaginally, intravesically or transdermally.

Pharmaceutical compositions suitable for oral administration can be solids or liquids and can, for example, be in the form of tablets, pills, dragees, gelatin capsules, solutions, syrups, and the like.

To this end the active ingredient may be mixed with an inert diluent or a non-toxic pharmaceutically acceptable carrier such as starch or lactose. Optionally, these pharmaceutical compositions can also contain a binder such as microcrystalline cellulose, gum tragacanth or gelatine, a disintegrant such as alginic acid, a lubricant such as magnesium stearate, a glidant such as colloidal silicon dioxide, a sweetener such as sucrose or saccharin, or colouring agents or a flavouring agent such as peppermint or methyl salicylate.

The invention also contemplates compositions which can release the active substance in a controlled manner. Pharmaceutical compositions which can be used for parenteral administration are in conventional form such as aqueous or oily solutions or suspensions generally contained in ampoules, disposable syringes, glass or plastics vials or infusion containers.

In addition to the active ingredient, these solutions or suspensions can optionally also contain a sterile diluent such as water for injection, a physiological saline solution, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

These pharmaceutical forms are prepared using methods which are routinely used by pharmacists.

The amount of active ingredient in the pharmaceutical compositions can fall within a wide range of concentrations and depends on a variety of factors such as the patient's sex, age, weight and medical condition, as well as on the method of administration. Thus the quantity of compound of formula I in compositions for oral administration is at least 0.5% by weight and can be up to 80% by weight with respect to the total weight of the composition.

For the preferred oral compositions, the daily dosage is in the range 0.01 to 1000 milligrams (mg) of compounds of formula I or II.

In compositions for parenteral administration, the quantity of compound of formula I or II present is at least 0.5% by weight and can be up to 33% by weight with respect to the total weight of the composition. For the preferred parenteral compositions, the dosage unit is in the range 0.01 mg to 1000 mg of compounds of formula I or II.

The daily dose can fall within a wide range of dosage units of compound of formula I or II and is generally in the range 0.01 to 1000 mg. However, it should be understood that the specific doses can be adapted to particular cases depending on the individual requirements, at the physician's discretion.

The following examples are provided for illustrative purposes only and are not intended, nor should they be construed, as limiting the invention in any manner. Those skilled in the art will appreciate that routine variations and modifications of the following examples can be made without exceeding the spirit or scope of the invention.

Analytical characterization of the compounds: Unless otherwise specified in the examples, characterization of the compounds was performed according to the following methods:

NMR spectra are recorded on a BRUKER AC 250 Fourier Transform NMR Spectrometer fitted with an Aspect 3000 computer and a 5 mm $^1H/^{13}C$ dual probehead or BRUKER DRX 400 FT NMR fitted with a SG Indigo$^2$ computer and a 5 mm inverse geometry $^1H/^{13}C/^{15}N$ triple probehead. The compound is studied in DMSO-$d_6$ (or CDCl$_3$) solution at a probe temperature of 313 K and at concentrations ranging from 2 to 20 mg/mil. The instrument is locked on the deuterium signal of DMSO-$d_6$ (or CDCl$_3$). Chemical shifts are given in ppm downfield from TMS taken as internal standard. DMSO-$d_6$ (deuterated dimethyl sulfoxide).

Mass spectrometric measurements in LC/MS mode are performed as follows:

HPLC Conditions

Analyses are performed using a WATERS Alliance HPLC system mounted with an INEFRTSIL ODS 3-, DP 5 μm, 250×4.6 mm column.

The gradient runs from 100% solvent A (acetonitrile, water, TFA (10/90/0.1, v/v/v)) to 100% solvent B (acetonitrile, water, TFA (90/10/0.1, v/v/v)) in 7 min with a hold at 100% B of 4 min. The flow rate is set at 2.5 ml/min and a split of 1/10 is used just before API source. The chromatography is carried out at 30° C.

MS Conditions

Samples are dissolved in acetonitrile/water, 70/30, v/v at the concentration of about 250 μg/ml. API spectra (+or −) are performed using a FINNIGAN (San Jose, Calif., USA) LCQ ion trap mass spectrometer. APCI source operates at 450° C. and the capillary heater at 160° C. ESI source operates at 3.5 kV and the capillary heater at 210° C.

Mass spectrometric measurements in EI/DIP mode are performed as follows: samples are vaporized by heating the probe from 50° C. to 250° C. in 5 min. EI (Electron Impact) spectra are recorded using a FINNIGAN (San Jose, Calif., USA) TSQ 700 tandem quadrupole mass spectrometer. The source temperature is set at 150° C.

Specific rotation is recorded on a Perkin-Elmer MC241 or MC341 polarimeter. The angle of rotation is recorded at 25° C. on 1% solutions in MeOH. For some molecules, the solvent is CH$_2$Cl$_2$ or DMSO, due to solubility problems.

Water content is determined using a Metrohm microcoulometric Karl Fischer titrator.

Preparative chromatographic separations are performed on silicagel 60 Merck, particle size 15-40 µm, reference 1.15111.9025, using in-house modified Jobin Yvon-type axial compression columns (80 mm i.d.), flow rates between 70 and 150 ml/min. Amount of silicagel and solvent mixtures are as described in individual procedures.

Preparative chiral chromatographic separations are performed on a DAICEL Chiralpak AD 20 µm, 100*500 mm column using an in-house build instrument with various mixtures of lower alcohols and $C_5$ to $C_8$ linear, branched or cyclic alkanes at ±350 ml/min. Solvent mixtures are as described in individual procedures.

Melting points are determined on a Buchi 535 Totoli-type fusionometre, and are not corrected, or by the onset temperature on a Perkin Elmer DSC 7.

Unless specified otherwise in the examples, the compounds are obtained in the neutral form.

EXAMPLE 1

Synthesis of Ketones 1.1 [1-(methylsulfonyl)-4-piperidinyl](phenyl)methanone 1:

Neat DIPEA (1.54 ml, 8.86 mmol) was added dropwise to a solution of phenyl(4-piperidinyl)methanone hydrochloride (1 g, 4.43 mmol) in $CH_2Cl_2$ (20 ml) at 0° C. Then, neat MsCl (377 µL, 4.87 mmol) was slowly added and the cooling bath was removed. After 30 minutes, the reaction was quenched with water and diluted with $CH_2Cl_2$. After separation, the organic phase was washed with brine, dried over $MgSO_4$ and evaporated to dryness. The final ketone 1 was obtained as a white solid (1.16 g, 98%).

1.2 Cyclobutyl(2-pyridinyl)methanone 7:

To an etheral solution of cyclobutyl magnesium bromide (prepared from bromocyclobutane (970 mg, 7.18 mmol) and magnesium (175 mg, 7.18 mmol) in ether (20 ml)) was dropwise added a solution of 2-cyanopyridine (748 mg, 7.18 mmol) in ether (10 ml) at room temperature. After 2 hours, the reaction was quenched by addition of an aqueous saturated solution of $NH_4Cl$. The mixture was extracted with ether. The organic phase was dried over $MgSO_4$ and concentrated under vacuum. The residue was purified by chromatography on silica gel (hexane/AcOEt 95/5) to give the cyclobutyl(2-pyridinyl)methanone 7 as colorless oil (960 mg, 83%).

1.3 (5-Chloro-2-thienyl)(2-pyridinyl)methanone 8:

To an etheral solution of bromo(5-chloro-2-thienyl)magnesium (prepared from 2-bromo-5-chloro-thiophene (1.9 g, 9.62 mmol) and magnesium turnings (234 mg, 9.62 mmol) in ether (20 ml)) was dropwise added a solution of 2-cyanopyridine (1 g, 9.62 mmol) in ether (10 ml) at room temperature. After 2 hours, the reaction was quenched by addition of an aqueous saturated solution of $NH_4Cl$. The mixture was extracted with ether. The organic phase was dried over $MgSO_4$ and concentrated under vacuum. The residue was treated with a 2 N HCl solution at 90° C. during 30 minutes. The solution was neutralized by addition of a concentrated solution of NaOH and extracted with ether. The organic phase was dried over $MgSO_4$ and concentrated under vacuum. The residue was purified by chromatography on silica gel (hexane/AcOEt 90/10) to give the (5-chloro-2-thienyl)(2-pyridinyl)methanone 8 as a yellowish oil (1.13 g, 52%).

1.4 3,3-Dimethyl-1-(2-thienyl)-1-butanone 10:

A mixture of t-butylacetyl chloride (1 ml, 7.2 mmol), 2-(tributylstannyl)thiophene (2.4 ml, 7.56 mmol) and $PdCl_2(PPh_3)_2$ (98 mg, 0.14 mmol) in toluene (50 ml) was heated at reflux until the starting material disappeared. After cooling at room temperature, the brown-black solution was diluted with ether and washed with a 0.1 N aqueous HCl solution. The organic phase was separated and stirred vigorously with a 10% w/v aqueous KF solution for 30 minutes. After filtration, the layers were separated and the organic one washed with water, brine, dried over $MgSO_4$ and concentrated. The residual brown oil was chromatographied on silica gel (hexane/AcOEt 97/3) to give 3,3-dimethyl-1-(2-thienyl)-1-butanone 10 as a colorless oil (810 mg, 62%).

1.5 3,5,5-Trimethyl-1-(2-thienyl)-1-hexanone 11:

The title compound was synthesized according to the method described in 2.4.

3,5,5-trimethyl-1-(2-thienyl)-1-hexanone 11 was obtained as a colorless oil (670 mg, 57%).

1.6 Cycloheptyl(2-thienyl)methanone 13:

The title compound was synthesized according to the method described in 2.4.

Cycloheptyl(2-thienyl)methanone 13 was obtained as a colorless oil (708 mg, 16%).

1.7 2-Cyclopentyl-1-(2-thienyl)ethanone 15:

The title compound was synthesized according to the method described in 2.4.

2-Cyclopentyl-1-(2-thienyl)ethanone 15 was obtained as a colorless oil (701 mg, 70%).

1.8 Phenyl(tetrahydro-2H-thiopyran-4-yl)methanone 17:

Tetrahydro-2H-thiopyran-4-carbonitrile was synthesized as described in: Straessler C., Linden A., Heimgartner H., Helv. Chim. Acta (1997), 80 (5), 1528-1554.

Tetrahydro-2H-thiopyran-4-carbonitrile (2.6 g, 20.5 mmol) and CuI (195 mg, 1 mmol) were diluted in dry THF (200 ml). A 1M solution of phenyl magnesium bromide in THF (41 ml, 41 mmol) was added and the mixture was heated at reflux for 16 hours. After cooling at room temperature, ether was added and the imine was hydrolyzed with a 1 N HCl solution for 10 minutes. The organic phase was separated and treated with a 0.1 N HCl solution for 10 minutes. The organic phase was separated and washed with brine, dried over $MgSO_4$ and evaporated in vacuum. After chromatography on silica gel ($CH_2Cl_2$/hexane 30/70), the phenyl(tetrahydro-2H-thiopyran-4-yl)methanone 17 was obtained as a white solid (3 g, 70%).

1.9 Cycloheptyl(3-pyridinyl)methanone 18:

A solution of N-methoxy-N-methylcycloheptanecarboxamide (1.11 g, 6 mmol) in ether (10 ml) was added dropwise at −78° C. to a solution of 3-lithiopyridine (prepared by addition of BuLi (3.75 ml, 6 mmol) to 3-bromopyridine (0.58 ml, 6 mmol) in ether (25 ml) at −78° C.). The mixture was stirred for 2 hours at −78° C., quenched by addition of aqueous saturated $NH_4Cl$, allowed to warm to room temperature and diluted with ether. The layers were separated and the aqueous phase was extracted 3 times with ether. Combined organic layers were washed with brine, dried over $Na_2SO_4$ and concentrated. After purification by chromatography on silica gel ($CH_2Cl_2$), the cycloheptyl(3-pyridinyl)methanone 18 was obtained as a slightly yellow oil (490 mg, 40%).

1.10 4-Cyclohepten-1-yl(phenyl)methanone 21:

Methyl 4-cycloheptene-1-carboxylate was synthesized as described in: Chuit C., Tetrahedron (1972), 28, 4797-4813.

Methyl 4-cycloheptene-1-carboxylate (1.54 g, 10 mmol) and N,O-dimethyl hydroxylamine HCl (1.51 g, 15.5 mmol) were slurred in THF (20 ml) and cooled down to −20° C. under nitrogen. A solution of i-PrMgCl in THF (15 ml, 30 mmol) was added over 15 minutes maintaining the temperature below −5° C. The mixture was agitated for 20 minutes at −10° C. and quenched with 20% weight aqueous $NH_4Cl$. The product was extracted using ether and the organic phase was dried over $MgSO_4$ and concentrated. Purification by chromatography on silica gel ($CH_2Cl_2$) afforded the amide as a colorless oil (1.60 g, 89%).

The N-methoxy-N-methyl amide was dissolved in dry THF (10 ml) and cooled down to 0° C. A 3M etheral phenyl magnesium bromide solution (17.5 ml, 52.5 mmol) was added dropwise and then the mixture was heated at 65° C. for 1 hour. The mixture was cooled at room temperature and carefully treated with a 1 N HCl solution for 30 minutes at 40° C. The solution was diluted with ether and the organic phase separated, dried over $MgSO_4$ and concentrated. The residual oil was chromatographied on silica gel ($CH_2Cl_2$/hexane 10/90) and the 4-cyclohepten-1-yl(phenyl)methanone 21 was isolated as a colorless oil (1.35 g, 77%).

1.11 Phenyl(8-thiabicyclo[3.2.1]oct-3-yl)methanone 22:

8-thiabicyclo[3.2.1]octan-3-one was synthesized as described in Parr A. J., Walton N. J., Bensalem S., McCabe P. H., Routledge W., Phytochemistry (1991), 30 (8), 2607-2609.

A solution of tert-BuOK (2.41 g, 21.52 mmol) in t-BuOH/DME 1:2 (24 ml) was added at 0° C. to a solution of 8-thiabicyclo[3.2.1]octan-3-one (1.53 g, 10.75 mmol) and tosylmethyl isocyanide (2.3 g, 11.83 mmol) in DME (20 ml). The solution was stirred for 3 hours at room temperature. After addition of ether, the mixture was washed with a saturated aqueous $NaHCO_3$ solution, dried over $MgSO_4$ and evaporated. After purification by chromatography on silica gel (hexane/AcOEt 85/15), 8-thiabicyclo[3.2.1]octane-3-carbonitrile was obtained as a colorless oil (1.03 g, 63%).

A 3M etheral solution of phenyl magnesium bromide (6.72 ml, 20.16 mmol) was added at 0° C. to a solution of the above nitrile (1.03 g, 6.72 mmol) in dry THF (10 ml). After 30 minutes, the ice bath was removed and the reaction continued at room temperature for 16 hours. The reaction was carefully quenched by addition of a saturated aqueous $NH_4Cl$ solution. After addition of ether, organic layer was separated, washed with brine, dried over $MgSO_4$ and concentrated. The residual oil was chromatographied on silica gel (hexane/AcOEt 94/6) to give the phenyl(8-thiabicyclo[3.2.1]oct-3-yl)methanone 22 as a colorless oil (586 mg, 38%).

1.12 1-Cycloheptyl-2-butyn-1-one 23:

A solution of cycloheptanecarboxaldehyde (1.3 g, 10.3 mol) in THF (10 ml) was added dropwise at −70° C. to a solution of 1-propynylrthium (15.4 mmol). The mixture was stirred for 1 h15 at −70° C., quenched by addition of aqueous saturated ammonium chloride, allowed to warm to room temperature and diluted with ether. The layers were separated and the aqueous phase was extracted 3 times with ether. Combined organic layers were washed with brine, dried over $Na_2SO_4$ and concentrated. After purification by chromatography on silica gel (hexane/ether 80/20), the alcohol was obtained as a colorless oil (560 mg, 22%). This alcohol was oxidized using standard Swern's conditions to furnish after purification by chromatography on silica gel (hexane/AcOEt 97/3) the 1-cycloheptyl-2-butyn-1-one 23 as a colorless liquid (330 mg, 59%).

1.13 (2,2-Dimethyl-1,3-dioxan-5-yl)(phenyl)methanone 25:

Ethyl 2,2-dimethyl-1,3-dioxane-5-carboxylate was synthesized as described in: Dubois J., Foures C., Bory S., Falcou S., Gaudry M., Marquet A., Tetrahedron (1991), 47, 1001-1012.

The ethyl 2,2-dimethyl-1,3-dioxane-5-carboxylate (1.88 g, 10 mmol) and N,O-dimethyl hydroxylamine HCl (1.51 g, 15.5 mmol) were slurred in THF (20 ml) cooled to −20° C. under nitrogen. A solution of i-PrMgCl in THF (15 ml, 30 mmol) was added over 15 minutes maintaining the temperature below −5° C. The mixture was stirred for 20 minutes at −10° C. and quenched with 20% weight aqueous $NH_4Cl$. The product was extracted using ether and the organic phase was dried over $MgSO_4$ and concentrated to give a colorless oil (1.8 g, 90%).

The crude N-methoxy-N-methyl amide (1.8 g, 8.87 mmol) was dissolved in dry THF (25 ml) and cooled at 0° C. A 1M etheral phenyl magnesium bromide solution (27 ml, 27 mmol) was added dropwise and the reaction was allowed to reach room temperature. After 16 hours, the mixture was cooled at 0° C. and carefully treated with a 1 N HCl solution for 30 minutes at room temperature. The solution was diluted with ether and the organic phase separated, dried over $MgSO_4$ and concentrated. The residual oil was chromatographied on silica gel ($CH_2Cl_2$/hexane 25/750) and the (2,2-dimethyl-1,3-dioxan-5-yl)(phenyl)methanone 25 was isolated as a colorless oil (1.30 g, 80%).

1.14 tert-Butyl 4-benzoyl-1-piperidinecarboxylate 26:

Solid $(Boc)_2O$ (6.0 g, 27.4 mmol) was added portionwise, at room temperature, to 4-benzoyl piperidine hydrochloride (6.2 g, 27.4 mmol) dissolved in a mixture of dioxane (100 ml) and 1 N aqueous NaOH solution (55 ml). After 2 hours, the mixture was diluted with ether. After separation, the organic phase was washed with water, dried over $MgSO_4$ and concentrated in vacuum. The colorless oil solidified on standing at air to furnish tert-butyl 4-benzoyl-1-piperidinecarboxylate 26 as a white solid (7.8 g, 98%).

1.15 1-Cycloheptyl-3-(trimethylsilyl)-2-propyn-1-one 28:

To a solution of triethylsilylacetylene (4.78 ml, 14 mmol) in THF (10 ml) at −78° C. was added dropwise a solution of BuLi in hexane (8 ml, 13 mmol). After 30 minutes, the mixture was warmed to −10° C. and a solution of N-methoxy-N-methylcycloheptanecarboxamide (2 g, 10.8 mmol) in THF (10 ml) was added. The mixture was stirred for 30 minutes at −10° C., quenched by addition of aqueous saturated ammonium chloride, allowed to warm up to room temperature and diluted with ether. The layers were separated and the aqueous phase was extracted with ether. Combined organic layers were washed with brine, dried over $Na_2SO_4$ and concentrated. After purification by chromatography on silica gel (hexane/$CH_2Cl_2$ 90/10), the 1-cycloheptyl-3-(trimethylsilyl)-2-propyn-1-one 28 was obtained as a colorless liquid (1.74 g, 72%).

1.16 Cycloheptyl(1-methyl-1H-pyrrol-2-yl)methanone 30:

To a solution of cycloheptyl anhydride (4 g, 15 mmol) in dry ether (5 ml) was added a 1 M $ZnCl_2$ etheral solution (15 ml, 15 mmol) under nitrogen. The reaction mixture was stirred at room temperature for 10 minutes. Then, N-methylpyrole (4 ml, 45 mmol) was added in one portion. Stirring was continued at room temperature for 5 hours. Hydrolysis was performed by addition of water and the mixture is then diluted with ether. After separation of the two layers, the ether solution was washed with a 10% NaOH solution (3 times), with water (3 times), brine, dried over $MgSO_4$ and evaporated in vacuum to yield a viscous orange oil. Purification by chromatography on silica gel ($CH_2Cl_2$/hexane 80/20) gave the cycloheptyl(1-methyl-1H-pyrrol-2-yl)methanone 30 as a colorless oil (701 mg, 23%).

1.17 Phenyl[4-(3-phenylpropoxy)phenyl]methanone 34:

Alkylation of the 4-hydroxyphenone was performed using the procedure described in: Goedheijt M. S., Hanson B. E., Reek J. N. H., Kamer P. C. J., Leeuwen P. W. N. M. van, J. Amer. Chem. Soc. (2000), 122 (8), 1650-1657. After purification the phenyl[4-(3-phenylpropoxy)phenyl]methanone 34 was obtained as a slightly orange solid (1.67 g, 53%).

1.18 (4-Fluorophenyl)(2-fluoro-3-pyridinyl)methanone 37:

A solution of 4-fluorobenzaldehyde (5.86 g, 45 mmol) in dry THF (10 ml) was dropwise added at −70° C. to a solution of 2-fluoro-3-lithiopyridine (prepared from 2-fluoropyridine (3.91 ml, 45 mmol) and LDA (49.5 mmol)) in THF (120 ml). After complete addition, the cooling bath was removed and the reaction was allowed to reach 10° C. Hydrolysis was performed by addition of water, and the mixture is then diluted with ether. After separation of the layers, the ether solution was washed with brine, dried over $Na_2SO_4$ and evaporated in vacuum to yield a viscous oil. The alcohol was dissolved in $CHCl_3$ (150 ml) and $MnO_2$ (58.62 g, 0.675 mol) was added at room temperature. After 16 hours, the mixture was filtered on a pad of Celite and concentrated. The residual oil was chromatographied on silica gel ($CH_2Cl_2$) and (4-fluorophenyl)(2-fluoro-3-pyridinyl)methanone 37 was isolated as a white solid (4.83 g, 49%).

1.19 (4-Fluorophenyl)(6-fluoro-3-pyridinyl)methanone 38:

6-fluoronicotinoyl chloride was prepared as described in: Anderson W. K., Dean D. C., Endo T., J. Med. Chem. (1990), 33 (6), 1667-1675.

A 2 M solution of 4-fluorophenyl magnesium chloride (7 ml, 14 mmol) was slowly added at −30° C. to a solution of 6-fluoronicotinoyl chloride (3.35 g, 21 mmol,) in ether (30 ml). After complete addition, the cooling bath was removed and the reaction was allowed to reach 10° C. Hydrolysis was performed by addition of water, and the mixture is then diluted with ether. After separation of the layers, the ether solution was washed with brine, dried over $Na_2SO_4$ and evaporated in vacuum to yield a yellow solid. After purification by chromatography on silica gel ($CH_2Cl_2$/Hexane 85/15), the (4-fluorophenyl)(6-fluoro-3-pyridinyl)methanone 38 was obtained as a white solid (1.52 g, 50%).

1.20 (6-Fluoro-3-pyridinyl)(phenyl)methanone 39:

A 3M etheral solution of phenyl magnesium chloride (4.67 ml, 14 mmol) was slowly added at −30° C. to a solution of 6-fluoronicotinoyl chloride (3.35 g, 21 mmol) in ether (25 ml). After complete addition, the cooling bath was removed and the reaction was allowed to reach 10° C. Hydrolysis was performed by addition of water, and the mixture is then diluted with ether. After separation of the layers, the ether solution was washed with brine, dried over $Na_2SO_4$ and evaporated in vacuum to yield a yellowish oil. After purification by chromatography on silica gel ($CH_2Cl_2$/Hexane 85/15), the (6-fluoro-3-pyridinyl)(phenyl)methanone 39 was obtained as a yellow oil (980 mg, 35%).

1.21 Cycloheptyl(2-fluoro-3-pyridinyl)methanone 40:

Cycloheptylcarboxaldehyde was prepared as described in: Reichardt C., Ferwanah A.-R., Pressler W., Yun K.-Y., Liebigs Ann. Chem. (1984), 4, 649-679.

A solution of cycloheptylcarboxaldehyde (1.89 g, 15 mmol) in dry THF (10 mL) was added dropwise at −70° C. to a solution of 2-fluoro-3-lithiopyridine (prepared from 2-fluoropyridine (1.3 ml, 15 mmol) and LDA (16.5 mmol); Guengoer T., Marsais F., Queguiner G., J. Organomet. Chem. (1981), 215 (2), 139-150) in THF (30 ml). After 2 h30 at −70° C., the reaction was stirred at room temperature during 16 hours. Hydrolysis was performed by addition of water, the mixture was then diluted with ether. After separation of the two layers, the ether solution was washed with brine, dried over $Na_2SO_4$ and evaporated in vacuum to yield a viscous oil. The alcohol was dissolved in $CH_2Cl_2$ (50 ml) at room temperature and PCC (6.46 g, 30 mmol) was added. After 16 hours, the mixture was filtered on a pad of Celite and concentrated. The residual oil was chromatographied on silica gel ($CH_2Cl_2$/hexane 75/25) and the cycloheptyl(2-fluoro-3-pyridinyl)methanone 40 was isolated as a colorless oil (780 mg, 24%).

1.22 Cycloheptyl(5-pyrimidinyl)methanone 42:

Cycloheptanecarboxaldehyde was prepared as described in Dubois J., Foures C., Bory S., Falcou S., Gaudry M., Marquet A., Tetrahedron (1991), 47, 1001-1012.

A solution of cycloheptanecarboxaldehyde (1.89 g, 15 mmol) in dry THF (10 ml) was added dropwise at −100° C. to a solution of 5-lithiopyrimidyl (prepared from 5-bromopyrimidine (2.16 g, 13.6 mmol) and BuLi (14 mmol) in THF (30 ml); Heinisch G., Holzer W., Langer T., Lukavsky P., Heterocycles (1996), 43 (1), 151-172). After 30 minutes at −100° C., hydrolysis was performed by addition of a 2.2 N etheral HCl solution at the same temperature. The cooling bath was removed and stirring was continued at room temperature for 1 hour. After dilution with water, the mixture was extracted with $CH_2Cl_2$. After separation of the layers, the organic solution was washed with brine, dried over $Na_2SO_4$ and evaporated in vacuum to yield a yellow oil. After purification by chromatography on silica gel ($CH_2Cl_2$/MeOH 95/5) the alcohol was isolated as a colorless oil (1.02 g, 36%). This alcohol was dissolved in $CHCl_3$ (20 ml) at room temperature and $MnO_2$ (6.44 g, 74.2 mmol) was added. After 24 hours, the mixture was filtered on a pad of Celite and concentrated. The residual oil was chromatographied on silica gel ($CH_2Cl_2$) and cycloheptyl(5-pyrimidinyl)methanone 42 was isolated as a white solid (360 mg, 36%).

Non commercial ketones described in Table 1 were used as intermediates for the synthesis of compounds of formula I and II

TABLE 1

| | ketones used as synthesis intermediates | |
|---|---|---|
| | | Analysis [or reference] |
| 1 | [1-(methylsulfonyl)-4-piperidinyl](phenyl)methanone | $^1$H NMR($CDCl_3$): 1.94(m, 4H); 2.81(s, 3H); 2.93-3.03(m, 2H); 3.41(m, 1H); 3.75(t, 1H); 3.80(t, 1H); 7.45-7.58(m, 3H); 7.90-7.93(m, 2H). |
| 2 | bis(3-methylphenyl)methanone | [Pickard, Vaughan, J. Amer. Chem. Soc. (1950), 72, 5017] |
| 3 | 2-ethyl-1-phenyl-1-butanone | [Rieke R. D., Hanson M. V., Brown J. D., Nium Q. J., J. Org. Chem. (1996), 61(8), 2726-2730] |
| 4 | 1-phenyl-4-penten-1-one | [Marvell E. N., Li T. H.-C., J. Amer. Chem. Soc. (1978), 100 (3), 883-888] |
| 5 | di(3-thienyl)methanone | [Strekowski L., Wydra R. L., Cegla M. T., Czarny A., Patterson S., J. Org. Chem. (1989), 54 (26), 6120-6123] |
| 6 | cyclopentyl(2-pyridinyl)methanone | [Patent DE 4304010] |
| 7 | cyclobutyl(2-pyridinyl)methanone | MS [M$^+$]: 161. |

TABLE 1-continued ketones used as synthesis intermediates

| | | Analysis [or reference] |
|---|---|---|
| 8 | (5-chloro-2-thienyl)(2-pyridinyl)methanone | MS [M$^+$]: 223/225. |
| 9 | 1-adamantyl(2-thienyl)methanone | [Sasaki T., Nakanishi A., Ohno M., J. Org. Chem. (1982), 47 (17), 3219-3224] |
| 10 | 3,3-dimethyl-1-(2-thienyl)-1-butanone | $^1$H NMR(CDCl$_3$): 0.85(m, 2H); 0.92(s, 9H); 1.03(d, 3H); 2.25(m, 1H); 2.70(dd, 1H); 2.85(dd, 1H); 7.11(dd, 1H); 7.60(d, 1H); 7.67(d, 1H). |
| 11 | 3,5,5-trimethyl-1-(2-thienyl)-1-hexanone | MS [M$^+$]: 182. |
| 12 | 2-ethyl-1-(2-thienyl)-1-hexanone | [Hartough, Kosak, J. Amer. Chem. Soc. (1947), 69, 3098] |
| 13 | cycloheptyl(2-thienyl)methanone | $^1$H NMR(CDCl$_3$): 1.54-1.79(m, 9H); 1.79-1.93(m, 2H); 3.25(m, 1H); 7.09-7.13(dd, 1H); 7.58-7.60(d, 1H); 7.68-7.69(d, 1H). |
| 14 | 2-propyl-1-(2-thienyl)-1-pentanone | [Abele E. M., Gol'dberg Y. S., Popelis Y. Y., Shimanskaya, M. V., J. Org. Chem. USSR (Engl. Transl.) (1990), 26 (8)., 1545-1550; Zh. Org. Khim. (1990), 26 (8), 1784-1790] |
| 15 | 2-cyclopentyl-1-(2-thienyl)ethanone | $^1$H NMR(CDCl$_3$): 1.22(m, 2H); 1.50-1.64(m, 4H); 1.8-1.95(m, 2H); 2.40(sept, 1H); 2.88-2.91(d, 2H); 7.09-7.13(dd, 1H); 7.59-7.61(d, 1H); 7.68-7.70(d, 1H). |
| 16 | (2,2,3,3-tetramethylcyclopropyl)(2-thienyl)methanone | (Huaxue Xuebao (1993) 51, 393-398) |
| 17 | phenyl(tetrahydro-2H-thiopyran-4-yl)methanone | MS [M$^+$]: 206. |
| 18 | cycloheptyl(3-pyridinyl)methanone | MS [M$^+$]: 203. |
| 19 | 1,4-dithiepan-6-yl(phenyl)methanone | [Murinov Y. I., Phosphorus Sulfur (1985), 23, 65-110] |
| 20 | bicyclo[3.2.1]oct-3-yl(phenyl)methanone | [Momose T., Muraoka O., Chem. Pharm. Bull. (1978), 26, 2217-2223] |
| 21 | 4-cyclohepten-1-yl(phenyl)methanone | $^1$H NMR(CDCl$_3$): 1.69-1.76(m, 2H); 1.94-2.02(m, 2H); 2.18-2.34(m, 4H); 3.51(m, 1H); 5.80(m, 2H); 7.42-7.53(m, 3H); 7.91-7.95(m, 2H). |
| 22 | phenyl(8-thiabicyclo[3.2.1]oct-3-yl)methanone | $^1$H NMR(CDCl$_3$): 1.90-2.25(m, 10H); 3.32(broad m, 2H); 3.70(m, 1H); 7.38-7.62(m, 3H); 7.85-7.95(m, 2H). |
| 23 | 1-cycloheptyl-2-butyn-1-one | MS [MH$^+$]: 165. |
| 24 | phenyl(pyrazolo[1,5-a]pyridin-3-yl)methanone | [Tanji K.- I., Sasahara T., Suzuki J., Higashino T., Heterocycles (1993), 35 (2), 915-924] |
| 25 | (2,2-dimethyl-1,3-dioxan-5-yl)(phenyl)methanone | $^1$H NMR(CDCl$_3$): 1.44(s, 3H); 1.51(s, 3H); 3.92-4.22(m, 5H); 7.45-7.58(m, 3H); 7.94-7.96(m, 2H). |
| 26 | tert-butyl 4-benzoyl-1-piperidinecarboxylate | MS [MH$^+$]: 290. |
| 27 | 4-isoquinolinyl(phenyl)methanone | [Ohba S., Sakamoto T., Yamanaka H., Heterocycles (1990), 31 (7), 1301-1308] |
| 28 | 1-cycloheptyl-3-(trimethylsilyl)-2-propyn-1-one | $^1$H NMR(CDCl$_3$): −0.01(s, 9H); 1.25-1.41(10H); 1.71-1.78(m, 2H); 2.35(m, 1H). |
| 29 | (1-methyl-1H-imidazol-2-yl)(phenyl)methanone | [Ohta S., Hayakawa S., Moriwaki H., Harada S., Okamoto M., Chem. Pharm. Bull. (1986), 34 (12), 4916-4926] |
| 30 | cycloheptyl(1-methyl-1H-pyrrol-2-yl)methanone | $^1$H NMR(CDCl$_3$): 1.51-1.90(m, 12H); 3.03(m, 1H); 3.67(m, 3H); 6.55(d, 2H); 7.20(bs, 1H). |
| 31 | 2,3-dihydro-1H-inden-5-yl(phenyl)methanone | [Baddeley, Gordon, J. Chem. Soc. (1952), 2190-2192] |
| 32 | phenyl(5,6,7,8-tetrahydro-2-naphthalenyl)methanone | [Arnold et al., J. Amer. Chem. Soc. (1950), 73, 4193] |
| 33 | phenyl(6,7,8,9-tetrahydro-5H-benzo[α]cyclohepten-2-yl)methanone | [Baddeley, Gordon, J. Chem. Soc. (1952), 2190-2192] |
| 34 | phenyl[4-(3-phenylpropoxy)phenyl]methanone | MS [M$^+$]: 316. |
| 35 | di(3-pyridinyl)methanone | [Sauter F., Stanetty P., Sittenthaler W., Waditschatka R., Monatsh. Chem. (1988), 119, 1427-1438] |
| 36 | (2-fluoro-3-pyridinyl)(phenyl)methanone | [Guengoer T., Marsais F. Queguiner G., J. Organomet. Chem. (1981), 215 (2), 139-150] |
| 37 | (4-fluorophenyl)(2-fluoro-3-pyridinyl)methanone | MS [M$^+$]: 219. |
| 38 | (4-fluorophenyl)(6-fluoro-3-pyridinyl)methanone | MS [M$^+$]: 219. |
| 39 | (6-fluoro-3-pyridinyl)(phenyl)methanone | $^1$H NMR(CDCl$_3$): 7.04-7.08(dd, 1H); 7.48-7.55(m, 2H); 7.60-7.67(m, 1H); 7.77-7.81(m, 2H); 8.23-8.28(dt, 1H); 8.64-8.65(broad d, 1H). |
| 40 | cycloheptyl(2-fluoro-3-pyridinyl)methanone | MS [M$^+$]: 221. |
| 41 | phenyl(5-pyrimidinyl)methanone | [Heinisch G., Holzer W., Langer T., Lukavsky P., Heterocycles (1996), 43 (1), 151-172] |
| 42 | cycloheptyl(5-pyrimidinyl)methanone | MS [M$^+$]: 204 |
| 43 | phenyl(3-pyridazinyl)methanone | [Heinisch G., Langer T., Synth. Commun. (1994), 24 (6), 773-778] |
| 44 | cycloheptyl(phenyl)methanone | Stadtmueller H., Greve B., Lennick K., Chair A., Knochel P., Synthesis (1995), 69-72. |

EXAMPLE 2

Synthesis of 2,2-diphenyl-3-butynenitrile 46

2.1 3,4-dibromo-2,2-diphenylbutanenitrile 45:

2,2-diphenyl-3-butenenitrile was synthesized as described in: Arumugam S., Verkade, J. G., J. Org. Chem. (1997), 62 (14), 4827-4828.

A solution of bromine (1.72 ml, 33.4 mmol) in carbon tetrachloride (50 ml) was added dropwise to a solution of 2,2-diphenyl-3-butenenitrile (6.1 g, 27.9 mmol) in carbon tetrachloride (250 ml) at room temperature. After 20 hours, the medium was diluted with ether and washed with a saturated aqueous $Na_2S_2O_3$ solution and brine. The organic phase was dried over $Na_2SO_4$ and evaporated to give 3,4-dibromo-2,2-diphenylbutanenitrile 45 as a slightly yellow waxy solid (11 g, quantitative) used directly for the next step.

2.2 2,2-diphenyl-3-butynenitrile 46:

A solution of 3,4-dibromo-2,2-diphenylbutanenitrile 45 (7.5 g, 19.8 mmol) in THF (50 ml) was added dropwise to a suspension of tert-BuOK (11.1 g, 99 mmol) in THF (250 ml) at −78° C. After 1 h30, the brown mixture was poured into a mixture of ether and a saturated aqueous $NH_4Cl$ solution. After separation, the organic phase was washed twice with water and finally with brine. Drying over $MgSO_4$ and evaporation gave an brown-orange oil which was chromatographied over silica gel (CH$_2$Cl$_2$/Hexane 25/75). The alkyne 46 was obtained as a slightly yellow oil (4 g, 93%).

$^1$H NMR (CDCl$_3$): 2.84 (s, 1H); 7.33-7.42 (m, 6H); 7.54-7.58 (m, 4H).

EXAMPLE 3

Synthesis of 3-ethynyl-1-azabicyclo[2.2.2]octane derivatives 3.1 (3R)-3-ethynyl-1-azabicyclo[2.2.2]octan-3-ol compound complexed with borane (1:1) 51

3.1.1 3-ethynylquinuclidin-3-ol 47:

Quinuclidinone (76 g, 0.608 mol) was added to a stirred suspension of lithium acetylide ethylene diamine complex (85.7 g, 0.791 mol) in dry THF (500 ml) under nitrogen, at 0° C. After 16 hours at room temperature, a saturated aqueous solution of K$_2$CO$_3$ was added and the mixture was extracted with THF (3 times). Organic phases were combined, dried over MgSO$_4$ and evaporated under vacuum. The white solid was triturated in ether, filtered and dried to give 3-ethynylquinuclidin-3-ol 47 (56.22 g, 61

3.1.2 (3R)-3-ethynyl-1-azabicyclo[2.2.2]oct-3-yl acetate 49:

3-ethynylquinuclidin-3-ol 47 (21 g, 138.6 mmol) was stirred with acetic anhydride (100 ml) at 120° C. for 5 hours. After cooling, the mixture was poured over ice then solid sodium carbonate was added (Caution: foaming) and stirring was continued for 1 hour. The mixture was extracted with ether (twice) and THF. The organic phases were combined and dried over MgSO$_4$. Evaporation of the solvent gave the acetate 48 (21.4 g, 82%) as an yellowish oil.

The enantiomers (400 g, 2.07 mol) were separated by MCC chromatography (Chiralpak AD column, heptane/ethanol/methanol 90/2/8, 23° C., 8 MCC columns (11.1*4.8 cm)) to give (3R)-3-ethynyl-1-azabicyclo[2.2.2]oct-3-yl acetate 49 as a white solid (first eluted enantiomer, 179 g, 45%).

MS (MH$^+$): 194.

3.1.3 (3R)-3-ethynyl-1-azabicyclo[2.2.2]octan-3-ol 50:

The acetate 49 (179 g, 0.926 mol) was treated with a solution of NaH (60% dispersion in oil, 100 mg, 2.7 mmol) in methanol (900 ml). After stirring for 2 hours at reflux, water (20 ml) was added and the solution concentrated. The residue was treated with ether and the white solid obtained was filtered off, dissolved in ethanol (2 L) and water (200 ml). The mixture was evaporated to dryness and dried under vacuum to give the (3R)-3-ethynyl-1-azabicyclo[2.2.2]octan-3-ol 50 as a white solid (138 g, 98%).

3.1.4 (3R)-3-ethynyl-1-azabicyclo[2.2.2]octan-3-ol compound complexed with borane (1:1) 51:

A suspension of the alcohol 50 (138 g, 0.912 mol) in THF (700 ml) at −10° C. was treated dropwise with a 1 M solution of BH$_3$.THF complex (1 1, 1 mol). After 30 minutes at 0° C., the reaction was warmed to 10° C. and then quenched by addition of water (500 ml). The mixture was extracted with AcOEt and the organic layer dried over MgSO$_4$. After evaporation of the solvent, the residue was crystallized from hot hexane/toluene (70/30) to afford the (3R)-3-ethynyl-1-azabicyclo[2.2.2]octan-3-ol compound complexed with borane (1:1) 51 as a white solid (142 g, 95%).

3.2 (3R)-3-ethynyl-1-azabicyclo[2.2.2]oct-3-yl methyl ether 53 (Method 0)

3.2.1 (3R)-3-ethynyl-3-methoxy-1-azabicyclo[2.2.2]octane with borane 52:

A solution of the amino-borane complex 51 (142 g, 0.86 mol) in THF (500 ml) was added dropwise to a suspension of NaH (60% dispersion in oil, 46 g, 0.946 mol) in THF (250 ml) at 0° C. After gas evolution, the reaction was continued at room temperature for 1 hour and the n-tetrabutylammonium iodide (7 g, 18 mmol) was then added. After 30 minutes, neat iodomethane (88 ml, 1.29 mol) was added dropwise. The reaction was followed by TLC (hexane/AcOEt 7/3). After completion of the reaction, a saturated aqueous NH$_4$Cl solution (500 ml) was added and the mixture extracted with ether. The organic phase was dried over MgSO$_4$ and evaporated. The crude product was crystallized from hot heptane to afford (3R-3-ethynyl-3-methoxy-1-azabicyclo[2.2.2]octane with borane (1:1) 52 as a white solid (120 g, 85%).

MS (MH$^+$-BH$_3$): 166.

3.2.2 (3R)-3-ethynyl-1-azabicyclo[2.2.2]oct-3-yl methyl ether 53:

A 5M HCl aqueous solution (100 ml) was added dropwise to a solution of the (3R)-3-ethynyl-3-methoxy-1-azabicyclo [2.2.2]octane with borane (1:1) 52 at −10° C.

The reaction was followed by LC (CH$_2$Cl$_2$/EtOH/NH$_4$OH 90/10/1). After completion of the reaction, the medium was neutralized by slow addition of solid potassium carbonate (control pH>8), extracted twice with AcOEt. The organic phases were combined and washed with brine, dried over MgSO$_4$ and evaporated. The free base 53 was obtained as a deliquescent white solid (22.6 g, 98%).

MS (MH$^+$): 166.

(3R)-3-ethoxy-3-ethynyl-1-azabicyclo[2.2.2]octane, (3R)-3-(benzyloxy)-3-ethynyl-1-azabicyclo[2.2.2]octane and (3R)-3-ethynyl-3-[(3-methylbenzyl)oxy-1-azabicyclo [2.2.2]octane (table 2) can be synthesized in an analogous way using respectively EtI, BnBr or 1-(bromomethyl)-3-methylbenzene instead of MeI.

TABLE 2

| 54 | (3R)-3-ethoxy-3-ethynyl-1-azabicyclo[2.2.2]octane | $^1$H NMR(CDCl$_3$): 1.2(t, 3H); 1.55-2.1(m, 4H); 2.27(pent, 1H); 2.42(s, 1H); 2.95(m, 4H); 3.1(dd, 1H); 3.25(dd, 1H); 3.40(pent, 1H); 3.62(pent, 1H). |
|---|---|---|
| 55 | (3R)-3-(benzyloxy)-3-ethynyl-1-azabicyclo[2.2.2]octane | $^1$H NMR(CDCl$_3$): 1.57-1.66(m, 1H); 1.80-1.91(m, 1H): 2.09-2.21(m, 2H); 2.39(pent, 1H); 2.65(s, 1H); 3.09(m, 4H); 3.25(dd, 1H); 3.30(dd, 1H); 4.58(d, 1H); 4.70(d, 1H); 7.26-7.39(m, 5H). |
| 56 | (3R)-3-ethynyl-3-[(3-methylbenzyl)oxy]-1-azabicyclo[2.2.2]octane | $^1$H NMR(CDCl$_3$): 1.55-1.70(m, 1H); 1.79-2.03(m, 1H); 2.08-2.20(m, 2H); 2.36(s, 3H); 2.39(m, 1H); 2.65(s, 1H); 3.01(m, 4H); 3.27(dd, 1H); 3.30(dd, 1H); 4.50(d, 1H); 4.67(d, 1H); 7.09-7.26(m, 4H). |

3.3 3-ethynyl-3-fluoroquinuclidine 57.

To a suspension of 3-ethynylquinuclidin-3-ol 47 (151 mg, 1 mmol) in CH$_2$Cl$_2$ (2 ml) at 0° C. was added neat DAST (132 Pl, 1 mmol) (DAST=diethylaminosulphur trifluoride).

After 30 minutes at 0° C., the reaction was quenched with water, and pH was made basic by addition of a saturated aqueous solution of K$_2$CO$_3$. The mixture was diluted with AcOEt, the organic phase was dried over Na$_2$CO$_3$ and evaporated. Chromatography on silica gel (CH$_2$Cl$_2$/MeOH 95/5) afforded the 3-ethynyl-3-fluoroquinuclidine 57 (77 mg, 50%).

EXAMPLE 4

Synthesis of Compounds of Formula I or II 4.1 1-cycloheptyl-3-[(3R)-3-methoxy-1-azabicyclo[2.2.2] oct-3-yl]-1-phenyl-2-propyn-1-ol 116, 117 and 118 (Method 1).

A 1.6 N solution of BuLi in hexane (41.7 ml, 66.7 mmol) was added dropwise to a solution of (3R)-3-ethynyl-1-azabicyclo[2.2.2]oct-3-yl methyl ether 53 (11 g, 66.7 mmol) in THF (100 ml) cooled at −5° C. After stirring for 10 minutes, the medium was cooled at −15° C., and a solution of cycloheptyl(phenyl)methanone 44 (14.2 g, 70.2 mmol) in THF (50 ml) was slowly added. The cooling bath was removed and the reaction was allowed to gradually warm to room temperature during 2 hours. The reaction was quenched by the addition of saturated aqueous NH$_4$Cl solution. The reaction mixture was washed with brine, dried over Na$_2$SO$_4$ and evaporated. The yellowish oil was purified by chromatography over silica gel (CH$_2$Cl$_2$/EtOH/NH$_4$OH 94/6/1). 1-cycloheptyl-3-[(3R)-3-methoxy-1-azabicyclo [2.2.2]oct-3-yl]-1-phenyl-2-propyn-1-ol 116 was obtained as a white solid (20.35 g, 83%, mixture of diastereomers).

After separation by chromatography on chiral phase (Chiralpak AD column, hexane/ethanol 90/10 DEA 0.1%), diastereomers 117 (second eluted) and 118 (first eluted) were obtained as white solids.

Absolute configurations were determined by single crystal X-Ray diffraction studies.

4.2 3-[(3R)-3-methoxy-1-azabicyclo[2.2.2]oct-3-yl]-1-phenyl-1-(3-pyridinyl)-1-ol 145, 146 and 147 (Method 2).

4.2.1 3-[(3R)-3-methoxy-1-azabicyclo[2.2.2]oct-3-yl]-1-phenyl-1-(3-pyridinyl)-2-propyn-1-ol 145: Mixture of Diastereoisomers.

A solution of the (3R)-3-ethynyl-1-azabicyclo[2.2.2]oct-3-yl methyl ether 53 (6.3 g, 38.2 mmol) in THF (100 ml) was cooled at 0° C. and a 1 N solution of EtMgBr in THF (40.4 ml, 40.4 mmol) was added dropwise, followed by the coaddition of a solution of phenyl(3-pyridinyl)methanone (7.7 g, 42 mmol) in THF (10 ml). The cooling bath was removed and the reaction evolved at room temperature for 2 hours. The reaction was then quenched by the addition of brine. After addition of AcOEt, the organic layer was separated, dried over Na$_2$SO$_4$ and evaporated to give a yellowish oil. The mixture of diastereomers 145 was obtained by crystallization from hot AcOEt as a slightly yellow solid (8 g, 60%).

4.2.2 3-[(3R)-3-methoxy-1-azabicyclo[2.2.2]oct-3-yl]-1-phenyl-1-(3-pyridinyl)-2-propynyl acetate 191 and 192.

A solution of the alcohol 145 (5.51 g, 15.8 mmol) and DMAP (772 mg, 6.3 mmol) in acetic anhydride (44.5 ml) was stirred at room temperature for 2 hours. The medium was poured on ice then neutralized by addition of solid Na$_2$CO$_3$ (control pH 7-8). Extraction with AcOEt, separation of phases and drying of the organic one over Na$_2$SO$_4$ gave the acetate (6.72 g, quantitative). After separation by chromatography on chiral phase (Chiralpak AD column, hexane/propanol/ethanol 90/8/2 DEA 0.1%), diastereomers were obtained as oils.

Compound 191: (1.89 g, 31%) first eluted, MS (MH$^+$): 391.

Compound 192: (2.01 g, 33%) second eluted, MS (MH$^+$): 391.

4.2.3 (1R)-3-[(3R)-3-methoxy-1-azabicyclo[2.2.2]oct-3-yl]-1-phenyl-1-propyn-1-ol 146:

A 5% methanolic solution of KOH (w/v) was added to the acetate 192 (9 g, 23.05 mmol) dissolved in methanol (135 ml) at room temperature, and was stirred for 1 h then quenched with brine. The mixture was extracted 3 times with AcOEt. The organic phase was dried over Na$_2$SO$_4$ and evaporated in vacuum. The pure product 146 was obtained after crystallization from hot AcOEt (5.57 g, 69%).

4.2.4 (1S)-3-[(3R)-3-methoxy-1-azabicyclo[2.2.2]oct-3-yl]-1-phenyl-1-(3-pyridiyl)-2-propyn-1-ol 147:

A 5% methanolic solution of KOH (w/v) was added to the acetate 191 (9 g, 23.05 mmol) dissolved in methanol (135 ml) at room temperature, and was stirred for 1 h then quenched with brine. The mixture was extracted 3 times with AcOEt. The organic phase was dried over Na$_2$SO$_4$ and evaporated in vacuum. The pure product 147 was obtained after crystallization from hot AcOEt (5.57 g, 69%).

4.3 3-[3-hydroxy-3-(4-methoxyphenyl)-3-(2-thienyl)-1-propynyl]quinuclidin-3-ol 152 (Method 3).

A 1.6 N solution of BuLi in hexane (1.12 ml, 1.79 mmol) was added dropwise to a solution of 3-ethynyl-1-azabicyclo [2.2.2]octan-3-ol 47 (123 mg, 0.81 mmol) in THF (5 ml) at room temperature. After stirring for 30 minutes, (4-methoxyphenyl)(2-thienyl)methanone (231 mg, 1.06 mmol, commercial) in THF (1 ml) was added slowly. After 2 hours, the reaction was quenched by addition of saturated aqueous NH$_4$Cl solution and diluted with AcOEt. The organic phase was washed with brine, dried over Na$_2$SO$_4$ and evaporated. The yellowish oil was purified by chromatography on silica gel (CH$_2$Cl$_2$/MeOH 85/15) and 3-[3-hydroxy-3-(4-methoxyphenyl)-3-(2-thienyl)-1-propynyl]quinuclidin-3-ol 152 was obtained as a white solid (41 mg, 14%, mixture of diastereomers).

4.4 (3R -3-13-hydroxy-3,3-di(2-thienyl)-1-propynyl]-3-methoxy-1-methyl-1-azoniabicyclo[2.2.2]octane iodide 155 (Method 4).

A solution of 3-[(3R)-3-methoxy-1-azabicyclo[2.2.2]oct-3-yl]-1,1-di(2-thienyl)-2-propyn-1-ol 154 (7.32 g, 20.36 mmol, synthesized as described in method 1) in acetone (150 ml) at room temperature was treated with iodomethane (1.39 ml, 22.40 mmol). After 20 minutes, the heterogeneous solution was cooled at 4° C. for 1 hour. Filtration afforded the ammonium 155 as a tan powder (9.56 g, 94%).

4.5 1-benzyl-3-(3-cyclohexyl-3-hydroxy-3-phenyl-1-propynyl)-3-methoxy-1-azoniabicyclo[2.2.2]octane bromide 96 (Method 5).

A solution of 1-cyclohexyl-3-(3-methoxy-1-azabicyclo [2.2.2]oct-3-yl)-1-phenyl-2-propyn-1-ol 104 (200 mg, 0.56 mmol) in a mixture of acetone/ether (v/v 2/3, 50 ml) was treated with benzyl bromide (0.67 ml, 5.6 mmol) at room temperature. After 45 minutes, the heterogeneous solution was cooled at 4° C. for 1 hour. Filtration and washing with ether (3 times) afforded the ammonium 96 as a white powder (235 mg, 80%).

MS (M): 444.

4.6 Methyl {[3-[(3R)-3-methoxy-1-azabicyclo[2.2.2]oct-3-yl]-1,1-di(2-thienyl)-2-propynyl]oxy}acetate (Method 6).

4.6.1 3-[(3R)-3-methoxy-1-azabicyclo[2.2.2]oct-3-yl]-1,1-di(2-thienyl)-2-propyn-1-ol Compound Complexed with Borane (1:1) 193.

A solution of 3-ethynyl-1-azabicyclo[2.2.2]oct-3-yl methyl ether compound complexed with borane 52 (1.10 g, 6.17 mmol) in THF (30 ml) was cooled at −40° C. A 1.6 N solution of BuLi in hexane (4.05 ml, 6.48 mmol) was then added dropwise. After stirring for 30 minutes, the medium was cooled at −30° C., and a solution of di-2-thienyl ketone (2.4 g, 12.35 mmol) in THF (10 ml) was slowly added. The cooling bath was removed and the reaction was allowed to gradually warm to 0° C. during 3 hours. The reaction was quenched by the addition of solid $Na_2SO_4.10H_2O$ (large excess). The reaction mixture was filtered and evaporated. The desired molecule was precipitated in an ether/hexane mixture and filtered off as a white solid (2.3 g, 96%).

MS ($MH^+$-$BH_3$): 374.

4.6.2 Methyl {[3-[(3R)-3-methoxy-1-azabicyclo[2.2.2]oct-3-yl]-1,1-di(2-thienyl)-2-propynyl]oxy}acetate Compound Complexed with Borane (1:1) 194.

A solution of the 3-[(3R)-3-methoxy-1-azabicyclo[2.2.2]oct-3-yl]-1,1-di(2-thienyl)-2-propyn-1-ol compound complexed with borane 193 (200 mg, 0.54 mmol) in THF (10 ml) under nitrogen and at room temperature was treated with NaH (60% dispersion in oil, 23 mg, 0.59 mmol). After 20 minutes, methyl bromoacetate (55 μL, 0.59 mmol) was added in one portion. After 16 hours, the reaction was quenched with water, and the mixture was then diluted with AcOEt. The organic phase was washed with brine, dried over $MgSO_4$ and evaporated to dryness to afford the methyl {[3-[(3R)-3-methoxy-1-azabicyclo[2.2.2]oct-3-yl]-1,1-di(2-thienyl)-2-propynyl]oxy}acetate compound complexed with borane (1:1) 194 as an oil (130 mg, 55%). This compound was used without other purification in the next step.

4.6.3 Methyl {[3-[(3R)-3-methoxy-1-azabicyclo[2.2.2]oct-3-yl]-1,1-di(2-thienyl)-2-propynyl]oxylacetate 156.

The acetate 194 was dissolved in a mixture of acetone/ether (20 ml/20 ml) and cooled at 0° C. TFA (2 ml) was added and the reaction was allowed to reach room temperature. After 20 minutes, the mixture was poured into a saturated aqueous $NaHCO_3$ solution and extraction was performed with AcOEt. The organic phase was dried with $MgSO_4$ and concentrated in vacuum. Purification by chromatography on silica gel ($CH_2Cl_2$/EtOH/$NH_4OH$ 95/5/0.1) afforded methyl {[3-[(3R)-3-methoxy-1-azabicyclo[2.2.2]oct-3-yl]-1,1-di(2-thienyl)-2-propynyl]oxy}acetate 156 as a colorless oil (84 mg, 66%).

4.7 3-(3-cyclohexyl-3-hydroxy-3-phenyl-1-propynyl)-1-azabicyclo[2.2.2]octan-3-ol 1-oxide 94 (Method 7).

A solution of 3-(3-cyclohexyl-3-hydroxy-3-phenyl-1-propynyl)quinuclidin-3-ol 99 (30 mg, 0.09 mmol) in EtOH (100 μL) at room temperature was treated with methyl trioxorhenium (0.7 mg, 0.0028 mmol) and hydrogen peroxide (100 μL). After 16 hours, the mixture was diluted with ether and washed with water and brine. After separation, the organic phase was evaporated under vacuum and afforded the N-oxide derivative 94 as a white powder (15 mg, 49%).

4.8 1-cyclohexyl-3-(3-fluoro-1-azabicyclo[2.2.2]oct-3-yl)-1-phenylprop-2-yn-1-ol 111 (Method 8).

A 1.6 N solution of BuLi in hexane (730 μA, 1.16 mmol) was added dropwise to a solution of 3-ethynyl-3-fluoroquinuclidine 57 (162 mg, 1.06 mmol) in THF (5 ml) at 0° C. After stirring for 30 minutes, cyclohexyl(phenyl)methanone (207 mg, 1.16 mmol) in THF (1 ml) was added slowly. After 30 minutes, the reaction was quenched by the addition of saturated aqueous $NH_4Cl$ solution and diluted with AcOEt. The organic phase was washed with brine, dried over $Na_2SO_4$ and evaporated. The residue was purified by chromatography over silica gel ($CH_2Cl_2$/MeOH 97.5/2.5) and 1-cyclohexyl-3-(3-fluoro-1-azabicyclo[2.2.2]oct-3-yl)-1-phenylprop-2-yn-1-ol 111 was obtained as colorless foam (mixture of diastereomers, 30 mg, 8%).

4.9 3-(3,3-diphenyl-1-butynyl)-1-azabicyclo[2.2.2]oct-3-yl methyl ether 65 (Method 9).

4.9.1 3-(3,3-diphenyl-1-butynyl)quinuclidin-3-ol 195:

(1-methyl-1-phenyl-2-propynyl)benzene (Dehmlow E., Tetrahedron Lett. (1971), 563-566) (380 mg, 1.84 mmol.) in THF (10 ml) at −78° C. was treated with a 1.6 N solution of BuLi in hexane (1.21 ml, 1.94 mmol). After 30 minutes, at the same temperature, a solution of quinuclidinone (300 mg, 2.4 mmol) in THF (5 ml) was added dropwise. After 1 hour, the reaction was left at room temperature for 12 hours. The mixture was then diluted with ether and washed with water (twice) and brine. The organic phase was dried over $MgSO_4$ and evaporated to dryness. Chromatography on silica gel (elution: $CH_2Cl_2$/EtOH/$NH_4OH$ 90/10/0.1) gave 3-(3,3-diphenyl-1-butynyl)quinuclidin-3-ol 195 as a white solid (380 mg, 61%). This compound was used as such in the next step.

4.9.2 3-(3,3-diphenyl-1-butynyl)-1-azabicyclo[2.2.2]oct-3-yl methyl ether Compound Complexed with Borane (1:1) 196:

3-(3,3-diphenyl-1-butynyl)quinuclidin-3-ol 195 (380 mg, 1.15 mmol) was dissolved in THF (20 ml) and cooled at −10° C. A solution of $BH_3$.THF (1.20 ml, 1.20 mmol) was added dropwise, and the reaction was followed by TLC. When all the starting material has disappeared, the reaction was quenched with water and diluted with ether. After separation, the organic phase was washed with brine, dried over $MgSO_4$ and evaporated. The crude amino borane complex (396 mg, 1.15 mmol) in solution in THF (10 ml) at room temperature and under nitrogen, was treated with NaH (60% dispersion in oil, 51 mg, 1.26 mmol) for 15 minutes. Then, solid n-tetrabutylammonium Iodide (9 mg, 0.023 mmol) and iodomethane (146 μL, 2.30 mmol) were added. After 1 hour at room temperature, the mixture was diluted with ether, washed with water and brine. The organic phase was dried over $MgSO_4$ and evaporated under vacuum. After chromatography on silica gel (eluant: $CH_2Cl_2$/hexane 50/50 then 75/25), 3-(3,3-diphenyl-1-butynyl)-1-azabicyclo[2.2.2]oct-3-yl methyl ether compound complexed with borane (1:1) 196 was obtained as a white solid (371 mg, 90%). This compound was used as such for next step.

4.9.3 3-(3,3-diphenyl-1-butynyl)-1-azabicyclo[2.2.2]oct-3-yl methyl ether 65:

The 3-(3,3-diphenyl-1-butynyl)-1-azabicyclo[2.2.2]oct-3-yl methyl ether compound complexed with borane (1:1) 196 (371 mg, 1.03 mmol) in an ether/acetone solution (15 mL/5 ml) was deprotected with TFA (1 ml) at room temperature. After 1 hour, the mixture was poured into a saturated aqueous $NaHCO_3$ solution. Extraction with ether, drying of the organic phase over $Na_2CO_3$ and evaporation to dryness gave a solid. After purification by chromatography on silica gel, the 3-(3,3-diphenyl-1-butynyl)-1-azabicyclo[2.2.2]oct-3-yl methyl ether 65 was obtained as a mixture of enantiomers (white solid, 234 mg, 97%).

4.10 4-(3-methoxy-1-azabicyclo[2.2.2]oct-3-yl)-2,2-diphenyl-3-butynenitrile 64 (Method 10).

4.10.1 4-(3-hydroxy-1-azabicyclo[2.2.2]oct-3-yl)-2,2-diphenyl-3-butynenitrile 197:

A solution of 2,2-diphenyl-3-butynenitrile 46 (510 mg, 2.35 mmol) in THF (50 ml) under nitrogen was cooled at −78° C. A 1.6 N solution of BuLi in hexane (41.7 ml, 66.7 mmol) was added dropwise, and after 5 minutes a solution of quinuclidinone (346 mg, 2.53 mmol) in THF (10 ml) was rapidly added. After 15 minutes, the reaction was quenched at −78° C. by the addition of saturated aqueous NH$_4$Cl solution, and diluted with ether. The organic layer was washed with water (twice) and brine, dried over solid Na$_2$CO$_3$ and evaporated in vacuum. The colorless oil was triturated in an ether/hexane (1/1) mixture. 4-(3-hydroxy-1-azabicyclo[2.2.2]oct-3-yl)-2,2-diphenyl-3-butynenitrile 197 was collected by filtration and obtained as a white solid (310 mg, 39%). This compound was used as such for next step.

4.10.2 4-(3-methoxy-1-azabicyclo[2.2.2]oct-3-yl)-2,2-diphenyl-3-butynenitrile Compound Complexed with Borane (1:1) 198:

4-(3-hydroxy-1-azabicyclo[2.2.2]oct-3-yl)-2,2-diphenyl-3-butynenitrile 197 (305 mg, 0.89 mmol) was dissolved in THF (25 ml) and cooled at −20° C. A solution of BH$_3$.THF (0.89 ml, 0.89 mmol) was added dropwise, and the reaction was followed by TLC. The reaction was quenched with water and dilute with ether after disappearance of the starting material. After separation, the organic phase was washed with brine, dried over MgSO$_4$ and evaporated. The crude amino borane complex (360 mg, 0.89 mmol) in solution in THF (50 ml) at room temperature and under nitrogen, was treated with NaH (60% dispersion in oil, 40 mg, 0.98 mmol) for 30 minutes. Then, solid n-tetrabutylammonium iodide (7 mg, 0.017 mmol) and iodomethane (111 µL, 1.8 mmol) were added. After 16 hours at room temperature, the mixture was diluted with ether, washed with water and brine. The organic phase was dried over MgSO$_4$ and evaporated under vacuum. After chromatography on silica gel (eluant: CH$_2$Cl$_2$/hexane 50/50 then 75/25), 4-(3-methoxy-1-azabicyclo[2.2.2]oct-3-yl)-2,2-diphenyl-3-butynenitrile compound complexed with borane (1:1) 198 was obtained as a waxy solid (295 mg, 90%). This compound was used as such for next step.

4.10.3 4-(3-methoxy-1-azabicyclo[2.2.2]oct-3-yl)-2,2-diphenyl-3-butynenitrile 64:

Deprotection of 4-(3-methoxy-1-azabicyclo[2.2.2]oct-3-yl)-2,2-diphenyl-3-butynenitrile compound complexed with borane (1:1) 198 was performed by treatment of a ether/acetone solution (25 ml/5 ml) of the amino borane complex (270 mg, 0.73 mmol) at 0° C. with TFA (1 ml). After 2 hours at 0° C., the ice bath was removed and the reaction was performed at room temperature for 2 hours. The mixture was poured into a saturated aqueous NaHCO$_3$ solution. Extraction with ether, drying of the organic phase over Na$_2$CO$_3$ and evaporation to dryness gave a viscous oil. After purification by chromatography over silica gel, 4-(3-methoxy-1-azabicyclo[2.2.2]oct-3-yl)-2,2-diphenyl-3-butynenitrile 64 was obtained as a mixture of enantiomers (colorless oil, 170 mg, 65%).

4.11 (3M-3-methoxy-3-(3-methoxy-3,3-diphenyl-1-propynyl)-1-azabicyclo[2.2.2]octane 62 (Method 11).

4.11.1 3-[(3R)-3-methoxy-1-azabicyclo[2.2.2]oct-3-yl]-1,1-diphenyl-2-propyn-1-ol Compound Complexed with Borane (1:1) 199:

A solution of 3-ethynyl-1-azabicyclo[2.2.2]oct-3-yl methyl ether compound complexed with borane 52 (1 g, 5.58 mmol) in THF (40 ml) was cooled at −40° C. A 1.6 N solution of BuLi in hexane (3.66 ml, 5.86 mmol) was added dropwise. After stirring for 30 minutes, the medium was cooled at −30° C., and a solution of benzophenone (2.03 g, 11.17 mmol) in THF (150 ml) was slowly added. The cooling bath was removed and the reaction was allowed to gradually warm to 0° C. during 5 hours. The reaction was quenched by the addition of saturated aqueous NH$_4$Cl solution. The reaction mixture was diluted with ether, washed with brine, dried over Na$_2$SO$_4$ and evaporated. The 3-[(3R)-3-methoxy-1-azabicyclo[2.2.2]oct-3-yl]-1,1-diphenyl-2-propyn-1-ol compound complexed with borane (1:1) 199 was precipitated in a mixture of ether/hexane, filtered off as a white solid (1.03 g, 50%) and used as such for next step.

4.11.2 (3R)-3-methoxy-3-(3-methoxy-3,3-diphenyl-1-propynyl)-1-azabicyclo[2.2.2]octane compound complexed with borane (1:1) 200:

A solution of the alcohol 199 (200 mg, 0.55 mmol) in THF (20 ml) under nitrogen and at room temperature was treated with NaH (24 mg, 0.61 mmol). After 20 minutes, iodomethane (37 µL, 0.61 mmol) was dropwise added. After 2 hours, the reaction was quenched with water and diluted with AcOEt. The organic phase was washed with brine, dried over MgSO$_4$ and evaporated to dryness to afford the methyl ether 200 as an oil (220 mg). This compound was used as such for next step.

4.11.3 (3R)-3-methoxy-3-(3-methoxy-3,3-diphenyl-1-propynyl)-1-azabicyclo[2.2.2]octane 62:

The methyl ether derivative 200 was dissolved in a mixture of acetone/ether (20 ml/20 ml) and cooled at 0° C. TFA (2 ml) was added and reaction was allowed to room temperature. After 45 minutes, the mixture was poured into a saturated aqueous NaHCO$_3$ solution and extracted with AcOEt. The organic phase was dried with MgSO$_4$ and concentrated in vacuum. Purification by chromatography on silica gel (CH$_2$Cl$_2$/EtOH/NH$_4$OH 92/8/0.1) afforded (3R)-3-methoxy-3-(3-methoxy-3,3-dipnenyl-1-propynyl]-1-azabicyclo[2.2.2]octane 62 as a white solid (107 mg, 54% for 2 steps).

4.12 (3R)-3-(3-cyclohexyl-3-fluoro-3-phenyl-1-propynyl)-3-methoxy-1-azabicyclo[2.2.2]octane fumarate 113 (Method 12).

1-cyclohexyl-3-[(3R)-3-methoxy-1-azabicyclo[2.2.2]oct-3-yl]-1-phenyl-2-propyn-1-ol 201 was prepared as described in 4.1 (method 1) using cyclohexyl(phenyl)methanone and (3R)-3-ethynyl-1-azabicyclo[2.2.2]oct-3-yl methyl ether 53.

Under argon, a solution of DAST (95 µL, 0.71 mmol) in CH$_2$Cl$_2$ (5 ml) was added to a cooled (-30° C.) solution of 1-cyclohexyl-3-[(3R)-3-methoxy-1-azabicyclo[2.2.2]oct-3-yl]-1-phenyl-2-propyn-1-ol 201 (250 mg, 0.71 mmol) in CH$_2$Cl$_2$ (20 ml). The reaction temperature was allowed to reach 10° C., then quenched with water and diluted with AcOEt. The organic phase was dried over MgSO$_4$ and evaporated to dryness leading to a colorless oil (160 mg, 63%). (3R)-3-(3-cyclohexyl-3-fluoro-3-phenyl-1-propynyl)-1-azabicyclo[2.2.2]oct-3-yl methyl ether (mixture of diastereomers) was converted into the corresponding fumaric salt 113 (using conventional methods) and obtained as a white solid (40 mg).

4.13 (3R)-3-(3-cyclohexyl-3-phenyl-1-propynyl)-1-azabicyclo[2.2.2]oct-3-yl methyl ether 112 (Method 13).

1-cyclohexyl-3-[(3R)-3-methoxy-1-azabicyclo[2.2.2]oct-3-yl]-1-phenyl-2-propyn-1-ol 201 (150 mg, 0.42 mmol) was dissolved under argon in CH$_2$Cl$_2$ (20 ml) and then cooled to −40° C. Neat Et$_3$SiH (203 µL, 1.27 mmol) was added dropwise. After 5 minutes, neat BF$_3$.OEt$_2$ (376 µL, 1.27 mmol) was slowly added to the mixture. After 15 minutes, the reaction was slowly left to room temperature, then quenched with saturated aqueous K$_2$CO$_3$ solution after 45 minutes and diluted with ether. The organic phase was dried over Na$_2$SO$_4$ and evaporated to dryness to give (3R)-3-(3-cyclohexyl-3-phenyl-1-propynyl)-1-azabicyclo[2.2.2]oct-3-yl methyl ether 112 (mixture of diastereomers) as a colorless oil (140 mg, 97%).

4.14 3-Cycloheptyl-1-[(3R)-3-methoxy-1-azabicyclo[2.2.2]oct-3-yl]-1,4-pentadiyn-3-ol 131 (Method 14).

3-cycloheptyl-1-[(3R-3-methoxy-1-azabicyclo[2.2.2]oct-3-yl]-5-(trimethylsilyl)-1,4-pentadiyn-3-ol 202 was prepared as described in 4.1 (method 1) using ketone 28 and (3R)-3-ethynyl-1-azabicyclo[2.2.2]oct-3-yl methyl ether 53, and obtained as a yellowish oil (2.86 g, 93%).

Deprotection was performed by dissolving the protected alkyne 202 (2.75 g, 8.7 mmol) in MeOH (50 ml) at room temperature. Solid K$_2$CO$_3$ (124 mg, 8.7 mmol) was added and the mixture was stirred for 2 hours. The solvent was removed and the residue was chromatographied on silica gel (elution: CH$_2$Cl$_2$/MeOH/NH$_4$OH 95/5/0.1) to give 3-cycloheptyl-1-[(3R)-3-methoxy-1-azabicyclo[2.2.2]oct-3-yl]-1,4-pentadiyn-3-ol 131 as a white solid (423 mg, 15%).

4.15 3-[(3R)-3-methoxy-1-azabicyclo[2.2.2]oct-3-yl]-1-phenyl-1-(4-piperidinyl)-2-propyn-1-ol 136 (Method 15).

Neat TFA (130 µL, 1.67 mmol) was added in one portion to a solution of tert-butyl-4-(1-hydroxy-3-[(3R)-3-methoxy-1-azabicyclo[2.2.2]oct-3-yl]-1-phenyl-2-propynyl}-1-piperidinecarboxylate 170 (190 mg, 0.42 mmol) in CH$_2$Cl$_2$ (5 ml) at 0° C. After 3 hours at the same temperature, the cooling bath was removed and the reaction warmed up at room temperature. After 10 hours, the reaction was diluted with ether and cooled at 0° C. A solution of NaHCO$_3$ was slowly added till pH was made basic. After separation, the organic layer was dried over Na$_2$CO$_3$ and evaporated in vacuum. The white solid was chromatographied on silica gel (elution: CH$_2$Cl$_2$/MeOH/NH$_4$OH 94/6/0.1) and 3-[(3R)-3-methoxy-1-azabicyclo[2.2.2]oct-3-yl]-1-phenyl-1-(4-piperidinyl)-2-propyn-1-ol 136 was obtained as a colorless semi-solid oil (mixture of diastereomers, 57 mg, 38%).

Table 3 lists the different compounds synthetized according to the methods specified in the last column and described here above.

TABLE 3

| | Salt | Configuration data | IUPAC Name | MS (MH+) | DSC (° C.) | method |
|---|---|---|---|---|---|---|
| 58 | | 3 | RAC | 3-{3-[(3-methylbenzyl)oxy]-1-azabicyclo[2.2.2]oct-3-yl}-1,1-diphenyl-2-propyn-1-ol | 438 | | 8 |
| 59 | | 3 | RAC | 3-(3-methoxy-1-azabicyclo[2.2.2]oct-3-yl)-1,1-diphenyl-2-propyn-1-ol | 348 | | 1 |
| 60 | | 3S | PURE | 3-[(3S)-3-methoxy-1-azabicyclo[2.2.2]oct-3-yl]-1,1-diphenyl-2-propyn-1-ol | 348 | | 1 |
| 61 | | 3R | PURE | 3-[(3R)-3-methoxy-1-azabicyclo[2.2.2]oct-3-yl]-1,1-diphenyl-2-propyn-1-ol | 348 | | 1 |
| 62 | | 3R | PURE | (3R)-3-methoxy-3-(3-methoxy-3,3-diphenyl-1-propynyl)-1-azabicyclo[2.2.2]octane | 362 | | 11 |
| 63 | | 3 | RAC | 3-(3-ethoxy-1-azabicyclo[2.2.2]oct-3-yl)-1,1-diphenyl-2-propyn-1-ol | 362 | | 1 |
| 64 | | 3 | RAC | 4-(3-methoxy-1-azabicyclo[2.2.2]oct-3-yl)-2,2-diphenyl-3-butynenitrile | 357 | | 10 |
| 65 | | 3 | RAC | 3-(3,3-diphenyl-1-butynyl)-1-azabicyclo[2.2.2]oct-3-yl methyl ether | 346 | | 9 |
| 66 | | 3R | PURE | methyl ({3-[(3R)-3-methoxy-1-azabicyclo[2.2.2]oct-3-yl]-1,1-diphenyl-2-propynyl}oxy)acetate | 420 | | 6 |
| 67 | | 1,3R | MIXT | 3-[(3R)-3-methoxy-1-azabicyclo[2.2.2]oct-3-yl]-1-(2-naphthyl)-1-phenyl-2-propyn-1-ol | 398 | | 1 |
| 68 | | 1,3R | MIXT | 1-(6-fluoro-3-pyridinyl)-3-[(3R)-3-methoxy-1-azabicyclo[2.2.2]oct-3-yl]-1-phenyl-2-propyn-1-ol | 367 | | 1 |
| 69 | | 1,3R | MIXT | 1-(4-isoquinolinyl)-3-[(3R)-3-methoxy-1-azabicyclo[2.2.2]oct-3-yl]-1-phenyl-2-propyn-1-ol | 399 | | 1 |
| 70 | | 3,3 | MIXT | 3-{3-[4-(dimethylamino)phenyl]-3-hydroxy-3-phenyl-1-propynyl}quinuclidin-3-ol | 377 | | 3 |
| 71 | | 3,3 | MIXT | 3-{3-[4-(dimethylamino)phenyl]-3-methoxy-3-phenyl-1-propynyl}quinuclidin-3-ol | 391 | | 3 |
| 72 | | 1,3R | MIXT | 3-[(3R)-3-methoxy-1-azabicyclo[2.2.2]oct-3-yl]-1-(3-methylphenyl)-1-phenylprop-2-yn-1-ol | 362 | | 1 |
| 73 | | 1,3 | MIXT | 3-(3-methoxy-1-azabicyclo[2.2.2]oct-3-yl)-1-(2-methoxyphenyl)-1-phenyl-2-propyn-1-ol | 378 | | 1 |
| 74 | | 1,3R | MIXT | 1-(2-fluoro-3-pyridinyl)-3-[(3R)-3-methoxy-1-azabicyclo[2.2.2]oct-3-yl]-1-phenyl-2-propyn-1-ol | 367 | | 1 |
| 75 | | 1,3 | MIXT | 3-[3-hydroxy-3-(5-nitro-2-furyl)-3-phenyl-1-propynyl]quinuclidin-3-ol | 369 | | 3 |
| 76 | | 1,3 | MIXT | 4-[1-hydroxy-3-(3-hydroxy-1-azabicyclo[2.2.2]oct-3-yl)-1-phenyl-2-propynyl]benzoic acid | 378 | | 3 |
| 77 | | 1,3 | MIXT | methyl 4-[1-hydroxy-3-(3-hydroxy-1-azabicyclo[2.2.2]oct-3-yl)-1-phenyl-2-propynyl]benzoate | 392 | | 3 |
| 78 | | 1,3R | MIXT | 3-[(3R)-3-methoxy-1-azabicyclo[2.2.2]oct-3-yl]-1-(1-methyl-1H-imidazol-2-yl)-1-phenyl-2-propyn-1-ol | 352 | | 1 |
| 79 | | 1,3R | MIXT | 3-[(3R)-3-methoxy-1-azabicyclo[2.2.2]oct-3-yl]-1-phenyl-1-pyrazolo[1,5-a]pyridin-3-yl-2-propyn-1-ol | 388 | | 1 |
| 80 | | 1,3R | MIXT | 1-(2,3-dihydro-1H-inden-5-yl)-3-[(3R)-3-methoxy-1-azabicyclo[2.2.2]oct-3-yl]-1-phenyl-2-propyn-1-ol | 388 | | 1 |
| 81 | | 1,3R | MIXT | 3-[(3R)-3-methoxy-1-azabicyclo[2.2.2]oct-3-yl]-1-phenyl-1-(5,6,7,8-tetrahydro-2-naphthalenyl)-2-propyn-1-ol | 402 | | 1 |
| 82 | | 1,3R | MIXT | 3-[(3R)-3-methoxy-1-azabicyclo[2.2.2]oct-3-yl]-1-phenyl-1-[4-(3-phenylpropoxy)phenyl]-2-propyn-1-ol | 482 | | 1 |
| 83 | | 1,3R | MIXT | 3-[(3R)-3-methoxy-1-azabicyclo[2.2.2]oct-3-yl]-1-phenyl-1-(6,7,8,9-tetrahydro-5H-benzo[a]cyclohepten-2-yl)-2-propyn-1-ol | 416 | | 1 |
| 84 | 1 fumarate | 1,3 | MIXT | 1-(3-methoxy-1-azabicyclo[2.2.2]oct-3-yl)-3-phenyl-1-heptyn-3-ol | 328 | | 1 |

TABLE 3-continued

| | Salt | Configuration data | | IUPAC Name | MS (MH+) | DSC (° C.) | method |
|---|---|---|---|---|---|---|---|
| 85 | | A-3§,3R | PURE | 1-[(3R)-3-methoxy-1-azabicyclo[2.2.2]oct-3-yl]-3-phenyl-1-heptyn-3-ol | 328 | | 1 |
| 86 | | B-3§,3R | PURE | 1-[(3R)-3-methoxy-1-azabicyclo[2.2.2]oct-3-yl]-3-phenyl-1-heptyn-3-ol | 328 | | 1 |
| 87 | | 1,3R | MIXT | 1-cyclopentyl-3-[(3R)-3-methoxy-1-azabicyclo[2.2.2]oct-3-yl]-1-phenyl-2-propyn-1-ol | 340 | | 1 |
| 88 | | 1,3R | MIXT | 1-cyclopentyl-3-[(3R)-3-methoxy-1-azabicyclo[2.2.2]oct-3-yl]-1-(2-pyridinyl)-2-propyn-1-ol | 341 | | 1 |
| 89 | | 1,3R | MIXT | 1-cyclooctyl-3-[(3R)-3-methoxy-1-azabicyclo[2.2.2]oct-3-yl]-1-phenyl-2-propyn-1-ol | 382 | | 1 |
| 90 | | B-1§,3R | PURE | 1-cyclooctyl-3-[(3R)-3-methoxy-1-azabicyclo[2.2.2]oct-3-yl]-1-phenyl-2-propyn-1-ol | 382 | | 1 |
| 91 | | A-1§,3R | PURE | 1-cyclooctyl-3-[(3R)-3-methoxy-1-azabicyclo[2.2.2]oct-3-yl]-1-phenyl-2-propyn-1-ol | 382 | | 1 |
| 92 | | 1,3 | MIXT | 3-(3-cyclohexyl-3-hydroxy-3-phenyl-1-propynyl)-3-hydroxy-1-methyl-1-azoniabicyclo[2.2.2]octane iodide | 354 | | 4 |
| 93 | | 1,3 | MIXT | 1-benzyl-3-(3-cyclohexyl-3-hydroxy-3-phenyl-1-propynyl)-3-hydroxy-1-azoniabicyclo[2.2.2]octane bromide | 430 | | 5 |
| 94 | | 1,3 | MIXT | 3-(3-cyclohexyl-3-hydroxy-3-phenyl-1-propynyl)quinuclidin-3-ol 1-oxide | 356 | | 7 |
| 95 | | 1,3 | MIXT | 3-(3-cyclohexyl-3-hydroxy-3-phenyl-1-propynyl)-3-methoxy-1-methyl-1-azoniabicyclo[2.2.2]octane iodide | 368 | | 4 |
| 96 | | 1,3 | MIXT | 1-benzyl-3-(3-cyclohexyl-3-hydroxy-3-phenyl-1-propynyl)-3-methoxy-1-azoniabicyclo[2.2.2]octane bromide | 444 | | 5 |
| 97 | | 1,3 | MIXT | 1-cyclohexyl-3-{3-[(3-methylbenzyl)oxy]-1-azabicyclo[2.2.2]oct-3-yl}-1-phenyl-2-propyn-1-ol | 444 | | 8 |
| 98 | | 1,3 | MIXT | 3-[3-(benzyloxy)-1-azabicyclo[2.2.2]oct-3-yl]-1-cyclohexyl-1-phenyl-2-propyn-1-ol | 430 | | 1 |
| 99 | | 1,3 | MIXT | 3-(3-cyclohexyl-3-hydroxy-3-phenyl-1-propynyl)quinuclidin-3-ol | 340 | | 3 |
| 100 | | A-3§,3§ | PURE | 3-(3-cyclohexyl-3-hydroxy-3-phenyl-1-propynyl)quinuclidin-3-ol | 340 | | 3 |
| 101 | | B-3§,3§ | PURE | 3-(3-cyclohexyl-3-hydroxy-3-phenyl-1-propynyl)quinuclidin-3-ol | 340 | | 3 |
| 102 | | C-3§,3§ | PURE | 3-(3-cyclohexyl-3-hydroxy-3-phenyl-1-propynyl)quinuclidin-3-ol | 340 | | 3 |
| 103 | | D-3§,3§ | PURE | 3-(3-cyclohexyl-3-hydroxy-3-phenyl-1-propynyl)quinuclidin-3-ol | 340 | | 3 |
| 104 | | 1,3 | MIXT | 1-cyclohexyl-3-(3-methoxy-1-azabicyclo[2.2.2]oct-3-yl)-1-phenyl-2-propyn-1-ol | 354 | | 1 |
| 105 | 1 fumarate | A-1§,3§ | PURE | 1-cyclohexyl-3-(3-methoxy-1-azabicyclo[2.2.2]oct-3-yl)-1-phenyl-2-propyn-1-ol | 354 | | 1 |
| 106 | 1 fumarate | B-1§,3§ | PURE | 1-cyclohexyl-3-(3-methoxy-1-azabicyclo[2.2.2]oct-3-yl)-1-phenyl-2-propyn-1-ol | 354 | | 1 |
| 107 | 1 fumarate | C-1§,3§ | PURE | 1-cyclohexyl-3-(3-methoxy-1-azabicyclo[2.2.2]oct-3-yl)-1-phenyl-2-propyn-1-ol | 354 | | 1 |
| 108 | 1 fumarate | D-1§,3§ | PURE | 1-cyclohexyl-3-(3-methoxy-1-azabicyclo[2.2.2]oct-3-yl)-1-phenyl-2-propyn-1-ol | 354 | | 1 |
| 109 | | 1R,3R | PURE | (1R)-1-cyclohexyl-3-[(3R)-3-methoxy-1-azabicyclo[2.2.2]oct-3-yl]-1-phenyl-2-propyn-1-ol | 354 | | 1 |
| 110 | | 1S,3R | PURE | (1S)-1-cyclohexyl-3-[(3R)-3-methoxy-1-azabicyclo[2.2.2]oct-3-yl]-1-phenyl-2-propyn-1-ol | 354 | | 1 |
| 111 | | 1,3 | MIXT | 1-cyclohexyl-3-(3-fluoro-1-azabicyclo[2.2.2]oct-3-yl)-1-phenylprop-2-yn-1-ol | 342 | | 8 |
| 112 | | 3,3R | MIXT | (3R)-3-(3-cyclohexyl-3-phenyl-1-propynyl)-3-methoxy-1-azabicyclo[2.2.2]octane | 338 | | 13 |
| 113 | 1 fumarate | 3,3R | MIXT | (3R)-3-(3-cyclohexyl-3-fluoro-3-phenyl-1-propynyl)-3-methoxy-1-azabicyclo[2.2.2]octane | 356 | | 12 |
| 114 | | 3,3 | MIXT | 3-[3-cyclohexyl-3-(4-fluorophenyl)-3-hydroxy-1-propynyl]quinuclidin-3-ol | 358 | | 3 |
| 115 | | 1,3R | MIXT | 1-cyclohexyl-3-[(3R)-3-methoxy-1-azabicyclo[2.2.2]oct-3-yl]-1-(2-thienyl)-2-propyn-1-ol | 360 | | 1 |
| 116 | | 1,3R | MIXT | 1-cycloheptyl-3-[(3R)-3-methoxy-1-azabicyclo[2.2.2]oct-3-yl]-1-phenyl-2-propyn-1-ol | 368 | | 1 |
| 117 | | 1R,3R | PURE | (1R)-1-cycloheptyl-3-[(3R)-3-methoxy-1-azabicyclo[2.2.2]oct-3-yl]-1-phenyl-2-propyn-1-ol | 368 | 131.6 | 1 |
| 118 | | 1S,3R | PURE | (1S)-1-cycloheptyl-3-[(3R)-3-methoxy-1-azabicyclo[2.2.2]oct-3-yl]-1-phenyl-2-propyn-1-ol | 368 | 126.4 | 1 |
| 119 | | 3R,3R | PURE | (3R)-3-[(3R)-3-cycloheptyl-3-hydroxy-3-phenyl-1-propynyl]-3-methoxy-1-methyl-1-azoniabicyclo[2.2.2]octane iodide | 382 | | 6 |
| 120 | | 3R,3S | PURE | (3R)-3-[(3S)-3-cycloheptyl-3-hydroxy-3-phenyl-1-propynyl]-3-methoxy-1-methyl-1-azoniabicyclo[2.2.2]octane iodide | 382 | | 6 |
| 121 | | 1,3R | MIXT | 1-cycloheptyl-3-[(3R)-3-methoxy-1-azabicyclo[2.2.2]oct-3-yl]-1-(5-pyrimidinyl)-2-propyn-1-ol | 370 | | 1 |
| 122 | | 1,3R | MIXT | 1-cycloheptyl-3-[(3R)-3-methoxy-1-azabicyclo[2.2.2]oct-3-yl]-1-(3-pyridinyl)-2-propyn-1-ol | 369 | | 1 |
| 123 | | 1,3R | MIXT | 1-cycloheptyl-3-[(3R)-3-methoxy-1-azabicyclo[2.2.2]oct-3-yl]-1-(2-thienyl)-2-propyn-1-ol | 374 | | 1 |
| 124 | | 1,3R | MIXT | 1-cycloheptyl-1-(2-fluoro-3-pyridinyl)-3-[(3R)-3-methoxy-1-azabicyclo[2.2.2]oct-3-yl]-2-propyn-1-ol | 387 | | 1 |
| 125 | | 1,3R | MIXT | 1-cycloheptyl-3-[(3R)-3-methoxy-1-azabicyclo[2.2.2]oct-3-yl]-1-(1-methyl-1H-pyrrol-2-yl)-2-propyn-1-ol | 371 | | 1 |

TABLE 3-continued

| | Salt | Configuration data | | IUPAC Name | MS (MH+) | DSC (° C.) | method |
|---|---|---|---|---|---|---|---|
| 126 | | 1,3R | MIXT | 1-(4-cyclohepten-1-yl)-3-[(3R)-3-methoxy-1-azabicyclo[2.2.2]oct-3-yl]-1-phenyl-2-propyn-1-ol | 366 | | 1 |
| 127 | | 1,3R | MIXT | 1-cyclobutyl-3-[(3R)-3-methoxy-1-azabicyclo[2.2.2]oct-3-yl]-1-phenyl-2-propyn-1-ol | 326 | | 1 |
| 128 | | A-1§,3R | PURE | 1-cyclobutyl-3-[(3R)-3-methoxy-1-azabicyclo[2.2.2]oct-3-yl]-1-phenyl-2-propyn-1-ol | 326 | | 1 |
| 129 | | B-1§,3R | PURE | 1-cyclobutyl-3-[(3R)-3-methoxy-1-azabicyclo[2.2.2]oct-3-yl]-1-phenyl-2-propyn-1-ol | 326 | | 1 |
| 130 | | 1,3R | MIXT | 1-cyclobutyl-3-[(3R)-3-methoxy-1-azabicyclo[2.2.2]oct-3-yl]-1-(2-pyridinyl)-2-propyn-1-ol | 327 | | 1 |
| 131 | | 1,3R | MIXT | 3-cycloheptyl-1-[(3R)-3-methoxy-1-azabicyclo[2.2.2]oct-3-yl]-1,4-pentadiyn-3-ol | 316 | | 14 |
| 132 | | 2,3R | MIXT | 4-(3-methoxy-1-azabicyclo[2.2.2]oct-3-yl)-1,2-diphenyl-3-butyn-2-ol | 362 | | 1 |
| 133 | 1 fumarate | 3 | RAC | 2-benzyl-4-(3-methoxy-1-azabicyclo[2.2.2]oct-3-yl)-1-phenyl-3-butyn-2-ol | 376 | | 1 |
| 134 | | 1,3R | MIXT | 3-[(3R)-3-methoxy-1-azabicyclo[2.2.2]oct-3-yl]-1-phenyl-1-(5-pyrimidinyl)-2-propyn-1-ol | 350 | | 1 |
| 135 | | 1,3R | MIXT | 3-[(3R)-3-methoxy-1-azabicyclo[2.2.2]oct-3-yl]-1-phenyl-1-(4-pyridinyl)-2-propyn-1-ol | 349 | | 2 |
| 136 | | 1,3R | MIXT | 3-[(3R)-3-methoxy-1-azabicyclo[2.2.2]oct-3-yl]-1-phenyl-1-(4-piperidinyl)-2-propyn-1-ol | 355 | | 15 |
| 137 | 1 fumarate | A-3§ | PURE | 3-(3-methoxy-1-azabicyclo[2.2.2]oct-3-yl)-1,1-bis(4-methylphenyl)-2-propyn-1-ol | 376 | | 1 |
| 138 | 1 fumarate | B-3§ | PURE | 3-(3-methoxy-1-azabicyclo[2.2.2]oct-3-yl)-1,1-bis(4-methylphenyl)-2-propyn-1-ol | 376 | | 1 |
| 139 | | 1,3R | MIXT | 1-(4-fluorophenyl)-1-(6-fluoro-3-pyridinyl)-3-[(3R)-3-methoxy-1-azabicyclo[2.2.2]oct-3-yl]-2-propyn-1-ol | 385 | | 1 |
| 140 | | 3 | RAC | 1,1-bis(4-fluorophenyl)-3-(3-methoxy-1-azabicyclo[2.2.2]oct-3-yl)-2-propyn-1-ol | 384 | | 1 |
| 141 | | 1,3R | MIXT | 1-(4-fluorophenyl)-1-(2-fluoro-3-pyridinyl)-3-[(3R)-3-methoxy-1-azabicyclo[2.2.2]oct-3-yl]-2-propyn-1-ol | 385 | | 1 |
| 142 | | 3 | RAC | 1,1-bis(4-chlorophenyl)-3-(3-methoxy-1-azabicyclo[2.2.2]oct-3-yl)-2-propyn-1-ol | 416/418/420 | | 1 |
| 143 | | 3R | PURE | 3-[(3R)-3-methoxy-1-azabicyclo[2.2.2]oct-3-yl]-1,1-di(3-thienyl)-2-propyn-1-ol | 360 | | 1 |
| 144 | | 1,3R | MIXT | 3-[(3R)-3-methoxy-1-azabicyclo[2.2.2]oct-3-yl]-1-phenyl-1-(3-pyridazinyl)-2-propyn-1-ol | 350 | | 1 |
| 145 | | 1,3R | MIXT | 3-[(3R)-3-methoxy-1-azabicyclo[2.2.2]oct-3-yl]-1-phenyl-1-(3-pyridinyl)-2-propyn-1-ol | 349 | | 2 |
| 146 | | 1R,3R | PURE | (1R)-3-[(3R)-3-methoxy-1-azabicyclo[2.2.2]oct-3-yl]-1-phenyl-1-(3-pyridinyl)-2-propyn-1-ol | 349 | 195 | 2 |
| 147 | | 1S,3R | PURE | (1S)-3-[(3R)-3-methoxy-1-azabicyclo[2.2.2]oct-3-yl]-1-phenyl-1-(3-pyridinyl)-2-propyn-1-ol | 349 | (162–163) | 2 |
| 148 | | 3R | PURE | 3-[(3R)-3-methoxy-1-azabicyclo[2.2.2]oct-3-yl]-1,1-di(3-pyridinyl)-2-propyn-1-ol | 350 | | 1 |
| 149 | | 3R | PURE | 3-[(3R)-3-methoxy-1-azabicyclo[2.2.2]oct-3-yl]-1,1-bis(3-methylphenyl)-2-propyn-1-ol | 376 | | 1 |
| 150 | | 3R | PURE | 1,1-bis(3-fluorophenyl)-3-[(3R)-3-methoxy-1-azabicyclo[2.2.2]oct-3-yl]-2-propyn-1-ol | 384 | | 1 |
| 151 | | 3R | PURE | 3-[(3R)-3-methoxy-1-azabicyclo[2.2.2]oct-3-yl]-1,1-bis[3-(trifluoromethyl)phenyl]-2-propyn-1-ol | 484 | | 1 |
| 152 | | 1,3 | MIXT | 3-[3-hydroxy-3-(4-methoxyphenyl)-3-(2-thienyl)-1-propynyl]quinuclidin-3-ol | 370 | | 3 |
| 153 | | 3 | RAC | 3-(3-methoxy-1-azabicyclo[2.2.2]oct-3-yl)-1,1-dithien-2-ylprop-2-yn-1-ol | 360 | | 1 |
| 154 | | 3R | PURE | 3-[(3R)-3-methoxy-1-azabicyclo[2.2.2]oct-3-yl]-1,1-di(2-thienyl)-2-propyn-1-ol | 360 | | 1 |
| 155 | | 3R | PURE | (3R)-3-[3-hydroxy-3,3-di(2-thienyl)-1-propynyl]-3-methoxy-1-methyl-1-azoniabicyclo[2.2.2]octane iodide | M+: 373 | 194 | 4 |
| 156 | | 3R | PURE | methyl {[3-[(3R)-3-methoxy-1-azabicyclo[2.2.2]oct-3-yl]-1,1-di(2-thienyl)-2-propynyl]oxy}acetate | 432 | | 6 |
| 157 | | 1,3R | MIXT | 3-[(3R)-3-methoxy-1-azabicyclo[2.2.2]oct-3-yl]-1-(2-pyridinyl)-1-(2-thienyl)-2-propyn-1-ol | 355 | | 1 |
| 158 | | 1,3R | MIXT | 3-[(3R)-3-methoxy-1-azabicyclo[2.2.2]oct-3-yl]-1-phenyl-1-pyridin-2-ylprop-2-yn-1-ol | 349 | | 1 |
| 159 | | A-1§,3R | PURE | 3-[(3R)-3-methoxy-1-azabicyclo[2.2.2]oct-3-yl]-1-phenyl-1-(2-pyridinyl)-2-propyn-1-ol | 349 | | 1 |
| 160 | | B-1§,3R | PURE | 3-[(3R)-3-methoxy-1-azabicyclo[2.2.2]oct-3-yl]-1-phenyl-1-(2-pyridinyl)-2-propyn-1-ol | 349 | | 1 |
| 161 | | 3R | PURE | 3-[(3R)-3-methoxy-1-azabicyclo[2.2.2]oct-3-yl]-1,1-dipyridin-2-ylprop-2-yn-1-ol | 350 | | 1 |
| 162 | | 1,3R | MIXT | 1-(1-adamantyl)-3-[(3R)-3-methoxy-1-azabicyclo[2.2.2]oct-3-yl]-1-phenyl-2-propyn-1-ol | 412 | | 1 |
| 163 | | 3 | RAC | 5-[(3-methoxy-1-azabicyclo[2.2.2]oct-3-yl)ethynyl]-5H-dibenzo[a,d]cyclohepten-5-ol | 372 | | 1 |

TABLE 3-continued

| Salt | Configuration data | | IUPAC Name | MS (MH+) | DSC (° C.) | method |
|---|---|---|---|---|---|---|
| 164 | 3 | RAC | 5-[(3-methoxy-1-azabicyclo[2.2.2]oct-3-yl)ethynyl]-10,11-dihydro-5H-dibenzo[a,d]cyclohepten-5-ol | 374 | | 1 |
| 165 | 3,3 | MIXT | 3-(3-bicyclo[2.2.1]hept-5-en-2-yl-3-hydroxy-3-phenyl-1-propynyl)quinuclidin-3-ol | 350 | | 3 |
| 166 | 1,3 | MIXT | 1-bicyclo[2.2.1]hept-5-en-2-yl-3-(3-methoxy-1-azabicyclo[2.2.2]oct-3-yl)-1-phenyl-2-propyn-1-ol | 364 | | 1 |
| 167 | 1,3 | MIXT | 3-(3-methoxy-1-azabicyclo[2.2.2]oct-3-yl)-1-[1-(methylsulfonyl)-4-piperidinyl]-1-phenyl-2-propyn-1-ol | 433 | | 1 |
| 168 | 3,3R | MIXT | 4-ethyl-1-[(3R)-3-methoxy-1-azabicyclo[2.2.2]oct-3-yl]-3-phenyl-1-hexyn-3-ol | 342 | | 1 |
| 169 | 3,3R | MIXT | 1-[(3R)-3-methoxy-1-azabicyclo[2.2.2]oct-3-yl]-3-phenyl-6-hepten-1-yn-3-ol | 326 | | 1 |
| 170 | 1,3R | MIXT | tert-butyl 4-{1-hydroxy-3-[(3R)-3-methoxy-1-azabicyclo[2.2.2]oct-3-yl]-1-phenyl-2-propynyl}-1-piperidinecarboxylate | 455 | | 1 |
| 171 | 1,3R | MIXT | 1-(2,2-dimethyl-1,3-dioxan-5-yl)-3-[(3R)-3-methoxy-1-azabicyclo[2.2.2]oct-3-yl]-1-phenyl-2-propyn-1-ol | 386 | | 1 |
| 172 | 1,3R | MIXT | 1-(1,4-dithiepan-6-yl)-3-[(3R)-3-methoxy-1-azabicyclo[2.2.2]oct-3-yl]-1-phenyl-2-propyn-1-ol | 404 | | 1 |
| 173 | 1,3R | MIXT | 3-[(3R)-3-methoxy-1-azabicyclo[2.2.2]oct-3-yl]-1-phenyl-1-tetrahydro-2H-thiopyran-4-yl-2-propyn-1-ol | 372 | | 1 |
| 174 | A-1§,3R | PURE | 3-[(3R)-3-methoxy-1-azabicyclo[2.2.2]oct-3-yl]-1-phenyl-1-tetrahydro-2H-thiopyran-4-yl-2-propyn-1-ol | 372 | | 1 |
| 175 | B-1§,3R | PURE | 3-[(3R)-3-methoxy-1-azabicyclo[2.2.2]oct-3-yl]-1-phenyl-1-tetrahydro-2H-thiopyran-4-yl-2-propyn-1-ol | 372 | | 1 |
| 176 | 1,3R | MIXT | 1-bicyclo[3.2.1]oct-3-yl-3-[(3R)-3-methoxy-1-azabicyclo[2.2.2]oct-3-yl]-1-phenyl-2-propyn-1-ol | 380 | | 1 |
| 177 | 1,3R | MIXT | 3-[(3R)-3-methoxy-1-azabicyclo[2.2.2]oct-3-yl]-1-phenyl-1-(8-thiabicyclo[3.2.1]oct-3-yl)-2-propyn-1-ol | 398 | | 1 |
| 178 | 3,3R | MIXT | 1-[(3R)-3-methoxy-1-azabicyclo[2.2.2]oct-3-yl]-3-phenyl-1-tetradecyn-3-ol | 426 | | 1 |
| 179 | 3,3R | MIXT | 1-[(3R)-3-methoxy-1-azabicyclo[2.2.2]oct-3-yl]-3-phenyl-1-decyn-3-ol | 370 | | 1 |
| 180 | 3,3R | MIXT | 1-[(3R)-3-methoxy-1-azabicyclo[2.2.2]oct-3-yl]-3-phenyl-1-octyn-3-ol | 342 | | 1 |
| 181 | 3,4,3R | MIXT | 4-hexyl-1-[(3R)-3-methoxy-1-azabicyclo[2.2.2]oct-3-yl]-3-phenyl-1-dodecyn-3-ol | 482 | | 1 |
| 182 | 3,3R | MIXT | 3-cycloheptyl-1-[(3R)-3-methoxy-1-azabicyclo[2.2.2]oct-3-yl]-1,4-hexadiyn-3-ol | 330 | | 1 |
| 183 | 3,3 | MIXT | 3-[(4E)-3-hydroxy-3-(4-methylphenyl)-5-(2-thienyl)-4-penten-1-ynyl]quinuclidin-3-ol | | | 3 |
| 184 | 3,5,3R | MIXT | 1-[(3R)-3-methoxy-1-azabicyclo[2.2.2]oct-3-yl]-5,7,7-trimethyl-3-(2-thienyl)-1-octyn-3-ol | 390 | | 1 |
| 185 | 3,3R | MIXT | 1-[(3R)-3-methoxy-1-azabicyclo[2.2.2]oct-3-yl]-5,5-dimethyl-3-(2-thienyl)-1-hexyn-3-ol | 348 | | 1 |
| 186 | 3,4,3R | MIXT | 4-ethyl-1-[(3R)-3-methoxy-1-azabicyclo[2.2.2]oct-3-yl]-3-(2-thienyl)-1-octyn-3-ol | 376 | | 1 |
| 187 | 3,3R | MIXT | 1-[(3R)-3-methoxy-1-azabicyclo[2.2.2]oct-3-yl]-4-propyl-3-(2-thienyl)-1-heptyn-3-ol | 376 | | 1 |
| 188 | 2,3R | MIXT | 1-cyclopentyl-4-[(3R)-3-methoxy-1-azabicyclo[2.2.2]oct-3-yl]-2-(2-thienyl)-3-butyn-2-ol | 361 | | 1 |
| 189 | 1,3R | MIXT | 3-[(3R)-3-methoxy-1-azabicyclo[2.2.2]oct-3-yl]-1-(2,2,3,3-tetramethylcyclopropyl)-1-(2-thienyl)-2-propyn-1-ol | 374 | | 1 |
| 190 | 1,3R | MIXT | 1-(5-chloro-2-thienyl)-3-[(3R)-3-methoxy-1-azabicyclo[2.2.2]oct-3-yl]-1-(2-pyridinyl)-2-propyn-1-ol | 389/391 | | 1 |
| 191 | A-3R,1§ | PURE | 3-[(3R)-3-methoxy-1-azabicyclo[2.2.2]oct-3-yl]-1-phenyl-1-(3-pyridinyl)-2-propynyl acetate | 391 | | 2 |
| 192 | B-3R,1§ | PURE | 3-[(3R)-3-methoxy-1-azabicyclo[2.2.2]oct-3-yl]-1-phenyl-1-(3-pyridinyl)-2-propynyl acetate | 391 | | 2 |
| 195 | 3 | RAC | 3-(3,3-diphenyl-1-butynyl)quinuclidin-3-ol | 332 | | 9 |
| 197 | 3 | RAC | 4-(3-hydroxy-1-azabicyclo[2.2.2]oct-3-yl)-2,2-diphenyl-3-butynenitrile | 343 | | 10 |
| 201 | 1,3R | MIXT | 1-cyclohexyl-3-[(3R)-3-methoxy-1-azabicyclo[2.2.2]oct-3-yl]-1-phenyl-2-propyn-1-ol | 354 | | 1 |
| 202 | 1,3R | MIXT | 3-cycloheptyl-1-[(3R)-3-methoxy-1-azabicyclo[2.2.2]oct-3-yl]-5-(trimethylsilyl)-1,4-pentadiyn-3-ol | 388 | | 1 |

EXAMPLE 5

(1R)-3-[(3R)-3-methoxy-1-azabicyclo[2.2.2]oct-3-yl]-1-phenyl-1-(3-pyridinyl)-2-propyn-1-ol (146) was converted into corresponding salts using conventional methods. As an example of such methods, compound 146 was converted into its methanesulfonic salt as described herafter. Neat methanesulfonic acid (46.5 μl, 0.717 mmol) was added dropwise to a solution of free base 146 (250 mg, 0.717 mmol) in distilled THF (20 ml). After 5 minutes, the salt was precipitated by addition of diethylether. The resulting white solid was filtered and dried under vacuum. (3R)-3-[(3R)-3-hydroxy-3-phenyl-3-(3-pyridinyl)-1-propynyl]-3-methoxy-1-azoniabicyclo[2.2.2]octane methanesulfonate was obtained as a white solid (215 mg) and was very hygroscopic.

Following salts were synthesized according to the same procedure: (1R)-3-[(3R)-3-methoxy-1-azabicyclo[2.2.2]oct- 3-yl]-1-phenyl-1-(3-pyridinyl)-2-propyn-1-ol dihydrochloride; (1R)-3-[(3R)-3-methoxy-1-azabicyclo[2.2.2]oct-3-yl]-1-phenyl-1-(3-pyridinyl)-2-propyn-1-ol hydrochloride; (3R)-3-[(3R)-3-hydroxy-3-phenyl-3-(3-pyridiniumyl)-1-propynyl]-3-methoxy-1-azoniabicyclo[2.2.2]octane sulfate; (3R)-3-[(3R)-3-hydroxy-3-phenyl-3-(3-pyridinyl)-1-propynyl]-3-methoxy-1-azoniabicyclo[2.2.2]octane methanesulfonate; (3R)-3-[(3R)-3-hydroxy-3-phenyl-3-(3-pyridiniumyl)-1-propynyl]-3-methoxy-1-azoniabicyclo[2.2.2]octane maleate.

EXAMPLE 6

Experimental Protocols of In Vitro Pharmacological Testing 6.1 Affinity for Human Muscarinic Receptors.
6.1.1 Cell Culture:
Chinese Hamster Ovarian cells (CHO) expressing the human recombinant m1, m2, m3, m4 and m5 receptor were cultured in Ham's F12 media supplemented with 100 μU/ml of penicillin, 100 μg/ml of streptomycin, 400 μg/ml of geneticin and 5% of fetal bovine serum. Cell cultures were maintained in a humidified incubator at 37° C. and 5% $CO_2$.
6.1.2 Membrane Preparation
Confluent CHO cells expressing human m1, m2, m3, m4 and m5 muscarinic receptors were harvested and resuspended in phosphate buffered saline without calcium and magnesium. The cell suspension was centrifuged at 1500×g for 3 min (4° C.). The cell pellet was homogenized in a 15 mM Tris-HCl (pH 7.5) buffer containing 2 mM $MgCl_2$, 0.3 mM EDTA and 1 mM EGTA. The crude membrane fraction was collected by two consecutive centrifugation steps at 40,000×g for 25 min (4° C.). The final pellet was resuspended, at a protein concentration ranging from 2 to 6 mg/ml, in a 7.5 mM Tris-HCl (pH 7.5) buffer containing 12.5 mM $MgCl_2$, 0.3 mM EDTA, 1 mM EGTA and 250 mM sucrose and stored in liquid nitrogen.
6.1.3 Binding Assay
Binding assays were performed according to procedure described in: Buckley N. J., Bonner T. I., Buckley C. M., Brann M. R., Mol. Pharmacol. (1989), 35, 469-476, but with slight modifications.
Briefly, 25 to 50 μg of membrane proteins were incubated at room temperature in 1 ml of a 50 mM Tris-HCl (pH 7.4) buffer containing 2 mM of $MgCl_2$, 0.1 nM of [$^3$H]-NMS (N-methylscopolamine, 85 Ci/mmol, from Apbiotech, UK) and increasing concentrations of test compound dissolved in DMSO (1% final concentration). Non specific binding was measured in the presence of 1 μM atropine. After 60 (m2) or 120 (m3) min. incubation, assays were stopped by rapid vacuum filtration of the samples through glass fiber filters (Filtermat A, Wallac, Belgium) presoaked in 0.3% polyethyleneimine for at least 2 h. Samples were further rinsed with 8 ml of ice-cold 50 mM Tris-HCl (pH 7.4) buffer. Radioactivity trapped onto the filter was counted in a Betaplate counter (Wallac). Competition binding curves were analyzed by non-linear regression with XLfit software (IDBS, UK).

Compounds according to the invention showed $pIC_{50}$ values ranging from 7 to 10 for the m3 and/or the m2 receptor. High affinities are especially shown by compounds 59, 61, 64, 72, 74, 80, 84, 85, 87, 89, 90, 91, 104, 107, 108, 109, 110, 111, 113, 115, 116, 117, 118, 119, 122, 123, 124, 126, 127, 128, 134, 135, 139, 140, 141, 142, 143, 145, 146, 150, 153, 154, 155, 162, 166, 168, 169, 172, 173, 174, 176, 177, 180, 185, 188 and 190.

6.2 Muscarinic M3-Receptor Antagonism on Isolated Guinea Pig Urinary Bladder.
Urinary bladder strips (Kachur J. F., Peterson J. S., Carter J. P., Rzeszotarski W. J., Hanson R. C., and Noronha-Blob L., J. Pharmacol. exp. Ther. (1988), 247, 867-872) were prepared from male Dunkin-Hartley guinea pigs. Tissues were mounted in 20 ml organ baths containing modified Krebs' solution. The bathing solution was maintained at 37° C. and gassed with 95% $O_2$-5% $CO_2$. Tissues were allowed to equilibrate for a period of 45 min under a resting tension of 0.5 g. Isometric contractions were measured by force-displacement transducers (HSE K30) coupled to an IOX (EMKA Technologies) computer system capable of controlling automatic data acquisition and bath washout by automatic fluid circulation through electrovalves at defined times. Drugs were manually injected into the bath. At the end of the 45 minutes stabilization period, tissues were contracted seven times with carbachol ($3.10^{-6}$ M) at 5 minutes intervals. Five cumulative concentration-response curves to carbachol ($10^{-8}$ to maximum $10^{-2}$ M) were constructed successively in the absence or presence of the test compound (incubation time: 1 hour). Results were obtained from at least 3 or 4 individual experiments testing pairs of ileum and urinary bladder from the same animal. Control tissues were treated with the solvent. Antagonistic activity of the test compound was estimated by the calculation of $pD'_2$ and/or $pA_2$ values according to the methods described in: Van Rossum J. M., Hurkmans J. A. T. M., Wolters C. J. J., Arch. Int. Pharmacodyn. Ther. (1963), 143, 299-330 and in: Arunlakshana O. & Schild H. O., Br. J. Pharmacol. (1959), 14, 48-58.

Compounds according to the invention showed $pA_2$ values of 8 and greater.

In the tables, the stereochemical information is contained in the two columns headed 'configuration data'. The second column indicates whether a compound has no stereogenic center (ACHIRAL), is a pure enantiomer (PURE), a racemate (RAC) or is a mixture of two or more stereoisomers, possibly in unequal proportions (MIE). The first column contains the stereochemical assignment for each recognised center, following the IUPAC numbering used in the preceding column. A number alone indicates the existence of both configurations at that center. A number followed by 'R' or 'S' indicates the known absolute configuration at that center. A number followed by '§' indicates the existence of only one but unknown absolute configuration at that center. The letter (A, B, C, D) in front is a way of distinguishing the various enantiomers or racemates of the same structure.

In the tables, the melting points are in most cases determined by the onset of the DSC curve. When a visual (fusionometer) melting point is given, the value is in parenthesis.

The invention claimed is:
1. A compound of formula I or II, or a pharmaceutically acceptable salt thereof,

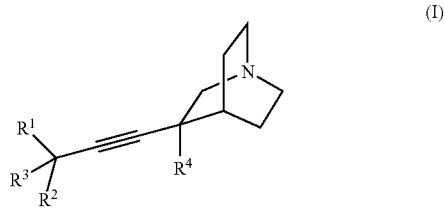

(I)

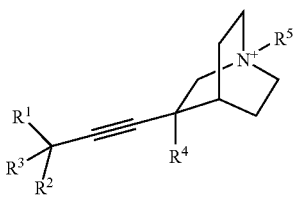

(II)

wherein
R¹ is hydrogen, halogen, alkyl, cyano, hydroxy or an oxy derivative;
R² is alkyl, alkenyl, alkynyl, aryl, heterocycle or aralkyl;
R³ is alkynyl, aryl, heterocycle or aralkyl;
R⁴ is hydroxy, halogen or an oxy derivative;
R⁵ is oxygen, alkyl or aralkyl;
R6 and R7 are the same or different and each is independently amido, alkyl, alkenyl, alkynyl, ester, ether, aryl, aralkyl, heterocycle or an oxy derivative, thio derivative, acyl derivative, amino derivative, sulfonyl derivative or sulfinyl derivative;
R6a is as defined for R6 except oxy derivative, thio derivative or amino derivative;
R6b is as defined for R6 except oxy derivative;
R6c is as defined for R6 except thio derivative;
R6d is as defined for R6 or is hydrogen;
R6e is as defined for R6;
R7e is as defined for R7;
R6f is as defined for R6 except for sulfonyl derivative;
R6g is as defined for R6 except for sulfinyl derivative;
R6h is as defined for R6;
R7h is as defined for R7;
R⁸ is C1-12-straight or branched alkylene, or C2-12-straight or branched alkenylene or alkynylene groups; and wherein
the term "alkyl" is defined as selected from the group consisting of saturated, monovalent carbon radicals having straight, branched or cyclic moieties or combinations thereof and containing 1 to 20 carbon atoms and includes alkyl moieties optionally substituted by 1 to 5 substituents selected from the group consisting of halogen, hydroxy, thiol, amino, nitro, cyano;
the term "alkenyl" is defined as selected from the group consisting of straight or cyclic, branched or unbranched, or unsaturated hydrocarbon radicals having at least one double bond and being optionally substituted by at least one substituent selected from the group consisting of halogen, hydroxy, thiol, amino, nitro, cyano, aryl and heterocycle;
the term "alkynyl" is defined as selected from the group consisting of straight or cyclic, branched or unbranched, or unsaturated hydrocarbon radical containing at least one carbon-carbon triple bond and being optionally substituted by at least one substituent selected from the group consisting of halogen, hydroxy, thiol, amino, nitro, cyano, trimethylsilyl, aryl and heterocycle;
the term "aryl" is defined as selected from the group consisting of an organic moiety derived from an aromatic hydrocarbon consisting of 1-3 rings and containing 6-30 carbon atoms by removal of one hydrogen, optionally substituted by 1 to 5 substituents selected from the group consisting of halogen, hydroxy, thiol, amino, nitro, cyano, acyl derivative, sulfonyl, sulfinyl, alkylamino, carboxy, ester, ether, amido, azido, sulfonic acid, sulfonamide, alkylsulfonyl, alkylsulfinyl, alkylthio, oxyester, oxyamido and aryl;

the term "heterocycle" is defined as selected from the group consisting of an aromatic or non aromatic cyclic alkyl, alkenyl, or alkynyl moiety, having at least one O, S and/or N atom interrupting the carbocyclic ring structure in which optionally, one of the carbon of the carbocyclic ring structure may be replaced by a carbonyl and optionally substituted by 1 to 5 substituents selected from the group consisting of halogen, hydroxy, thiol, amino, nitro, cyano, 5-pyrimidinyl, 3-pyridinyl, 4-pyridinyl, 3-thienyl, 2-thienyl, 5-chloro-2-thienyl, 1,4-dithiepan-6-yl, thiomorpholino-4-yl, 8-thiabicyclo (3.2.1)oct-3-yl, 2-pyridinyl, 2-fluoro-3-pyridinyl, 6-fluoro-3-pyridinyl, 4-isoquinolinyl, 5-nitro-2-furyl, 1-methyl-1H-imidazol-2-yl, 1-pyrazolo[1,5-a]pyridine-3-yl-, 1-methyl-1H-pyrrol-2-yl), 4-piperidinyl, (2,2-dimethyl-1,3-dioxan-5-yl, tetrahydro-2H-thiopyran-4-yl, 1-(methylsulfonyl)-4-piperidinyl, and 3-pyridazinyl;

or the term "heterocycle" is defined as an aromatic or non aromatic cyclic alkyl, alkenyl, or alkynyl moiety as defined above, having at least one O, S and/or N atom interrupting the carbocyclic ring structure and optionally, one of the carbon of the carbocyclic ring structure may be replaced by a carbonyl, wherein the aromatic heterocycles comprise pyridyl, furyl, pyrrolyl, thienyl, isothiazolyl, imidazolyl, benzimidazolyl, tetrazolyl, quinazolinyl, quinolizinyl, naphthyridinyl, pyridazinyl, pyrimidinyl, pyrazinyl, quinolyl, isociuinolyl, isobenzofuranyl, benzothienyl, pyrazolyl, indolyl, indolizinyl, purinyl, isoindolyl, carbazolyl, thiazolyl, 1,2,4-thiadiazolyl, thieno(2,3-b)furanyl, furopyranyl, benzofuranyl, benzoxepinyl, isooxazolyl, oxazolyl, thianthrenyl, benzothiazolyl, benzoxazolyl, cinnolinyl, phthalazinyl, quinoxalinyl, phenanthridinyl, acridinyl, perimidinyl, phenanthrolinyl, phenothiazinyl, furazanyl, isochromanyl, indolinyl, xanthenyl, hypoxanthinyl, pteridinyl, 5-azacytidinyl, 5-azauracilyl, triazolopyridinyl, imidazolopyridinyl, pyrrolopyrimidinyl, and pyrazolopyrimidinyl optionally substituted by alkyl or as described above for the term "alkyl", and wherein the non aromatic heterocycles comprise tetrahydrofuranyl, tetrahydropyranyl, piperidinyl, piperidyl, piperazinyl, imidazolidinyl, morpholino, morpholinyl, 1-oxaspiro (4.5)dec-2-yl, pyrrolidinyl, 2-oxo-pyrrolidinyl, 8-thia bicyclo[3.2.1.]cyclooctanyl, 1,4-dithiepanyl, tetrahydro-2H-thiopyranyl, optionally be substituted with any suitable groups, including but not limited to one or more moieties selected from lower alkyl, or other groups as described above for the term "alkyl";

or the term "heterocycle" comprise bicylic, tricyclic and tetracyclic, spiro groups in which any of the above heterocylic rings is fused to one or two rings independently selected from an aryl ring, a cycloalkane ring, a cycloalkene ring or another monocyclic heterocyclic ring or where a monocyclic heterocyclic group is bridged by an alkylene group, comprising quinuclidinyl, 7-azabicyclo(2.2.1)heptanyl, 7-oxabicyclo(2.2.1) heptanyl, and 8-azabicyclo(3.2.1)octanyl;

the term "aralkyl" represents a group of formula —R⁸-aryl;

the term "ester" is defined as a group of formula —COO-R6a;

the term amido" is defined as a group of formula —CONH2 or —CONHR6h or —CONR6hR7h;

the term "oxy derivative" is defined as an —O-R6b group selected from the group consisting of alkoxy, alkenyloxy, alkynyloxy, acyloxy, esteroxy, amidooxy, alkylsulfonyloxy, alkylsulfinyloxy, arylsulfonyloxy, arylsulfinyloxy, aryloxy, aralkoxy or heterocyclooxy;

the term "thio derivative" is defined as an —S-R6e group selected from the group consisting of alkylthio, alkenylthio, alkynylthio and arylthio;

the term "acyl derivative" is defined as a group of the formula R6d-CO— selected from the group consisting of hydrogen, formyl, acetyl, propionyl, isobutyryl, valeryl, lauroyl, heptanedioyl, cyclohexanecarbonyl, crotonoyl, fumaroyl, acryloyl, benzoyl, naphthoyl, furoyl, nicotinoyl, 4-carboxybutanoyl, oxalyl, ethoxalyl, cysteinyl, and oxamoyl;

the term "amino derivative" is defined as an —NHR6e or —NR6eR7e group selected from the group consisting of mono- or di-alkyl-, alkenyl-, alkynyl- and arylamino or mixed amino;

the term "sulfonyl derivative" is defined as a group of the formula —SO$_2$-R6f selected from the group consisting of alkylsulfonyl, alkenylsulfonyl, alkynylsulfonyl and arylsulfonyl;

the term "sulfinyl derivative" is defined as a group of the formula —SO-R6g selected from the group consisting of alkylsulfinyl, alkenylsulfinyl, alkynylsulfinyl and arylsulfinyl.

2. The compound according to claim 1, wherein $R^1$ is hydrogen, fluor, methyl, cyano, hydroxy, methoxy, —OCH$_2$COOCH$_3$ or —OC(=O)CCH$_3$.

3. The compound according to claim 1, wherein $R^2$ is alkyl, alkenyl, aryl, heterocycle or aralkyl.

4. The compound according to claim 1, wherein $R^3$ is alkynyl, aryl, heterocycle or benzyl.

5. The compound according to claim 1, wherein $R^4$ is hydroxy, fluoro, methoxy, ethoxy, benzyloxy or (3-methylbenzyl)oxy.

6. The compound according to claim 1, wherein $R^5$ is oxygen, methyl, or benzyl.

7. The compound according to claim 1, wherein
   $R^1$ is hydrogen, fluor, methyl, cyano, hydroxy, —OCH$_3$ or —OCH$_2$COOCH$_3$;
   $R^2$ is alkyl, alkenyl, aryl, heterocycle or benzyl;
   $R^3$ is alkynyl, aryl, heterocycle or benzyl;
   $R^4$ is hydroxy, fluoro, —OCH$_3$, —OCH$_2$CH$_3$ or —Obenzyl; and
   $R^5$ is oxygen, methyl or benzyl.

8. The compound according to claim 1, wherein the carbon atom to which $R^4$ is attached is in the "R" configuration.

9. A compound selected of the group consisting of
3-(3-methoxy-1-azabicyclo[2.2.2]oct-3-yl)-1,1-diphenyl-2-propyn-1-ol;
3-[(3R)-3-methoxy-1-azabicyclo[2.2.2]oct-3-yl]-1,1-diphenyl-2-propyn-1-ol;
4-(3-methoxy-1-azabicyclo[2.2.2]oct-3-yl)-2,2-diphenyl-3-butynenitrile;
3-[(3R)-3-methoxy-1-azabicyclo[2.2.2]oct-3-yl]-1-(3-methylphenyl)-1-phenylprop-2-yn-1-ol;
1-(2-fluoro-3-pyridinyl)-3-[(3R)-3-methoxy-1-azabicyclo[2.2.2]oct-3-yl]-1-phenyl-2-propyn-1-ol;
1-(2,3-dihydro-1H-inden-5-yl)-3-[(3R)-3-methoxy-1-azabicyclo[2.2.2]oct-3-yl]-1-phenyl-2-propyn-1-ol;
1-(3-methoxy-1-azabicyclo[2.2.2]oct-3-yl)-3-phenyl-1-heptyn-3-ol;
1-[(3R)-3-methoxy-1-azabicyclo[2.2.2]oct-3-yl]-3-phenyl-1-heptyn-3-ol;
1-cyclopentyl-3-[(3R)-3-methoxy-1-azabicyclo[2.2.2]oct-3-yl]-1-phenyl-2-propyn-1-ol;
1-cyclooctyl-3-[(3R)-3-methoxy-1-azabicyclo[2.2.2]oct-3-yl]-1-phenyl-2-propyn-1-ol;
1-cyclohexyl-3-(3-methoxy-1-azabicyclo[2.2.2]oct-3-yl)-1-phenyl-2-propyn-1-ol;
(1R)-1-cyclohexyl-3-[(3R)-3-methoxy-1-azabicyclo[2.2.2]oct-3-yl]-1-phenyl-2-propyn-1-ol;
(1S)-1-cyclohexyl-3-[(3R)-3-methoxy-1-azabicyclo[2.2.2]oct-3-yl]-1-phenyl-2-propyn-1-ol;
1-cyclohexyl-3-(3-fluoro-1-azabicyclo[2.2.2]oct-3-yl)-1-phenylprop-2-yn-1-ol;
(3R)-3-(3-cyclohexyl-3-fluoro-3-phenyl-1-propynyl)-3-methoxy-1-azabicyclo[2.2.2]octane;
1-cyclohexyl-3-[(3R)-3-methoxy-1-azabicyclo[2.2.2]oct-3-yl]-1-(2-thienyl)-2-propyn-1-ol;
1-cycloheptyl-3-[(3R)-3-methoxy-1-azabicyclo[2.2.2]oct-3-yl]-1-phenyl-2-propyn-1-ol;
(1R)-1-cycloheptyl-3-[(3R)-3-methoxy-1-azabicyclo[2.2.2]oct-3-yl]-1-phenyl-2-propyn-1-ol;
(1S)-1-cycloheptyl-3-[(3R)-3-methoxy-1-azabicyclo[2.2.2]oct-3-yl]-1-phenyl-2-propyn-1-ol;
(3R)-3-[(3R)-3-cycloheptyl-3-hydroxy-3-phenyl-1-propynyl]-3-methoxy-1-methyl-1-azoniabicyclo[2.2.2]octane iodide;
1-cycloheptyl-3-[(3R)-3-methoxy-1-azabicyclo[2.2.2]oct-3-yl]-1-(3-pyridinyl)-2-propyn-1-ol;
1-cycloheptyl-1-(2-fluoro-3-pyridinyl)-3-[(3R)-3-methoxy-1-azabicyclo[2.2.2]oct-3-yl]-2-propyn-1-ol;
1-(4-cyclohepten-1-yl)-3-[(3R)-3-methoxy-1-azabicyclo[2.2.2]oct-3-yl]-1-phenyl-2-propyn-1-ol;
1-cyclobutyl-3-[(3R)-3-methoxy-1-azabicyclo[2.2.2]oct-3-yl]-1-phenyl-2-propyn-1-ol;
3-[(3R)-3-methoxy-1-azabicyclo[2.2.2]oct-3-yl]-1-phenyl-1-(5-pyrimidinyl)-2-propyn-1-ol;
3-[(3R)-3-methoxy-1-azabicyclo[2.2.2]oct-3-yl]-1-phenyl-1-(4-pyridinyl)-2-propyn-1-ol;
1-(4-fluorophenyl)-1-(6-fluoro-3-pyridinyl)-3-[(3R)-3-methoxy-1-azabicyclo[2.2.2]oct-3-yl]-2-propyn-1-ol;
1,1-bis(4-fluorophenyl)-3-(3-methoxy-1-azabicyclo[2.2.2]oct-3-yl)-2-propyn-1-ol;
1-(4-fluorophenyl)-1-(2-fluoro-3-pyridinyl)-3-[(3R)-3-methoxy-1-azabicyclo[2.2.2]oct-3-yl]-2-propyn-1-ol;
1,1-bis(4-chlorophenyl)-3-(3-methoxy-1-azabicyclo[2.2.2]oct-3-yl)-2-propyn-1-ol;
3-[(3R)-3-methoxy-1-azabicyclo[2.2.2]oct-3-yl]-1,1-di(3-thienyl)-2-propyn-1-ol;
3-[(3R)-3-methoxy-1-azabicyclo[2.2.2]oct-3-yl]-1-phenyl-1-(3-pyridinyl)-2-propyn-1-ol;
(1R)-3-[(3R)-3-methoxy-1-azabicyclo[2.2.2]oct-3-yl]-1-phenyl-1-(3-pyridinyl)-2-propyn-1-ol;
1,1-bis(3-fluorophenyl)-3-[(3R)-3-methoxy-1-azabicyclo[2.2.2]oct-3-yl]-2-propyn-1-ol;
3-(3-methoxy-1-azabicyclo[2.2.2]oct-3-yl)-1,1-dithien-2-ylprop-2-yn-1-ol;
3-[(3R)-3-methoxy-1-azabicyclo[2.2.2]oct-3-yl]-1,1-di(2-thienyl)-2-propyn-1-ol;
(3R)-3-[3-hydroxy-3,3-di(2-thienyl)-1-propynyl]-3-methoxy-1-methyl-1-azoniabicyclo[2.2.2]octane iodide;
1-(1-adamantyl)-3-[(3R)-3-methoxy-1-azabicyclo[2.2.2]oct-3-yl]-1-phenyl-2-propyn-1-ol;
1-bicyclo[2.2.1]hept-5-en-2-yl-3-(3-methoxy-1-azabicyclo[2.2.2]oct-3-yl)-1-phenyl-2-propyn-1-ol;

4-ethyl-1-[(3R)-3-methoxy-1-azabicyclo[2.2.2]oct-3-yl]-3-phenyl-1-hexyn-3-ol;
1-[(3R)-3-methoxy-1-azabicyclo[2.2.2]oct-3-yl]-3-phenyl-6-hepten-1-yn-3-ol;
1-(1,4-dithiepan-6-yl)-3-[(3R)-3-methoxy-1-azabicyclo[2.2.2]oct-3-yl]-1-phenyl-2-propyn-1-ol;
3-[(3R)-3-methoxy-1-azabicyclo[2.2.2]oct-3-yl]-1-phenyl-1-tetrahydro-2H-thiopyran-4-yl-2-propyn-1-ol;
1-bicyclo[3.2.1]oct-3-yl-3-[(3R)-3-methoxy-1-azabicyclo[2.2.2]oct-3-yl]-1-phenyl-2-propyn-1-ol;
3-[(3R)-3-methoxy-1-azabicyclo[2.2.2]oct-3-yl]-1-phenyl-1-(8-thiabicyclo[3.2.1]oct-3-yl)-2-propyn-1-ol;
1-[(3R)-3-methoxy-1-azabicyclo[2.2.2]oct-3-yl]-3-phenyl-1-octyn-3-ol;
1-[(3R)-3-methoxy-1-azabicyclo[2.2.2]oct-3-yl]-5,5-dimethyl-3-(2-thienyl)-1-hexyn-3-ol;
1-cyclopentyl-4-[(3R)-3-methoxy-1-azabicyclo[2.2.2]oct-3-yl]-2-(2-thienyl)-3-butyn-2-ol;
1-(5-chloro-2-thienyl)-3-[(3R)-3-methoxy-1-azabicyclo[2.2.2]oct-3-yl]-1-(2-pyridinyl)-2-propyn-1-ol.

10. Pharmaceutical composition comprising a compound according to claim 1 and a pharmaceutical acceptable carrier.

11. Method for the treatment of symptoms in connection to lower urinary tract disorders or to disorders of lower and upper airways, which comprises administering an effective amount of the composition according to claim 10 to a patient in need thereof.

12. Method for the treatment of bladder disorders including urge and mixed urinary incontinence, pollakiuria, neurogenic or unstable bladder, overactive bladder and cystitis, which comprises administering an effective amount of the composition according to claim 10 to a patient in need thereof.

13. Synthesis intermediates of formula IIIbis, Vbis, V, VI, VIIbis, VII, VIII,

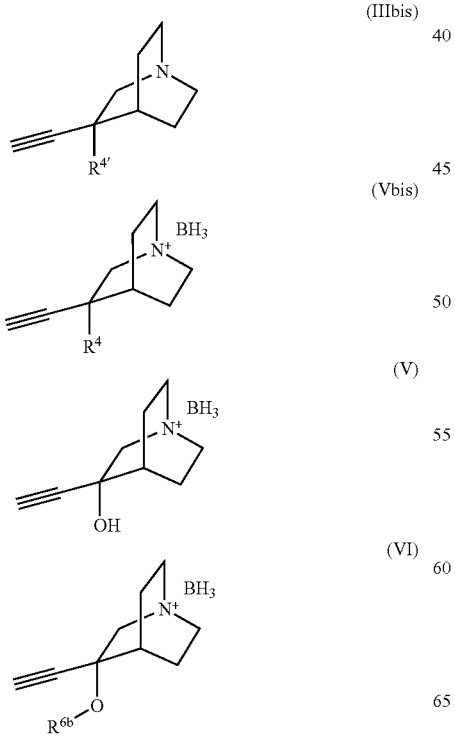

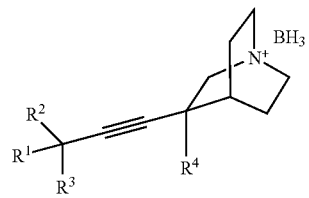

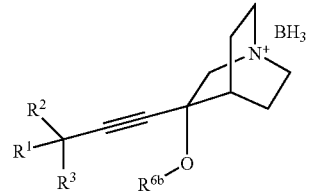

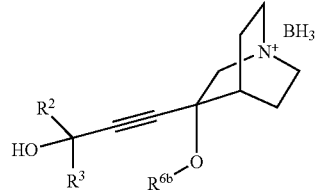

wherein
R¹ is hydrogen, halogen, alkyl, cyano, hydroxy or an oxy derivative;
R² is alkyl, alkenyl, alkynyl, aryl, heterocycle or aralkyl;
R³ is alkynyl, aryl, heterocycle or aralkyl;
R⁴' is halogen or an oxy derivative fluoro, —OCH3, —OEt, —O—CH2—C6H5, —O—CH2—(m-CH₃—C6H4);
R⁴ is hydroxy, halogen or an oxy derivative;
R6b is alkyl or aralkyl,
R⁸ is C1-12-straight or branched alkylene, or C2-12-straight or branched alkenylene or alkynylene groups; and wherein:
the term "alkyl" is defined as selected from the group consisting of saturated, monovalent carbon radicals having straight, branched or cyclic moieties or combinations thereof and containing 1 to 20 carbon atoms and includes alkyl moieties optionally substituted by 1 to 5 substituents selected from the group consisting of halogen, hydroxy, thiol, amino, nitro, and cyano;
the term "alkenyl" is defined as selected from the group consisting of straight or cyclic, branched or unbranched, or unsaturated hydrocarbon radicals having at least one double bond and being optionally substituted by at least one substituent selected from the group consisting of halogen, hydroxy, thiol, amino, nitro, cyano, aryl and heterocycle;
the term "alkynyl" is defined as selected from the group consisting of straight or cyclic, branched or unbranched, or unsaturated hydrocarbon radical containing at least one carbon-carbon triple bond and being optionally substituted by at least one substituent selected from the group consisting of halogen, hydroxy, thiol, amino, nitro, cyano, aryl and heterocycle;
the term "aryl" is defined as selected from the group consisting of an organic moiety derived from an aromatic hydrocarbon consisting of 1-3 rings and containing 6-30 carbon atoms by removal of one hydrogen, optionally substituted by 1 to 5 substituents selected from the group consisting of halogen, hydroxy, thiol, amino, nitro, cyano, acyl derivative, sulfonyl, sulfinyl, alkylamino, carboxy, ester, ether, amido, azido, sulfonic acid, sulfonamide, alkylsulfonyl, alkylsulfinyl, alkylthio, oxyester, oxyamido and aryl;

the term "heterocycle" is defined as selected from the group consisting of an aromatic or non aromatic cyclic alkyl, alkenyl, or alkynyl moiety, having at least one O, S and/or N atom interrupting the carbocyclic ring structure in which optionally, one of the carbon of the carbocyclic ring structure may be replaced by a carbonyl and optionally substituted by 1 to 5 substituents selected from the group consisting of halogen, hydroxy, thiol, amino, nitro, and cyano;

the term "aralkyl" represents a group of formula —$R^8$-aryl; and the term "oxy derivative" is defined as an —O-R6b group selected from the group consisting of alkoxy, alkenyloxy, alkynyloxy, acyloxy, esteroxy, amidooxy, alkylsulfonyloxy, alkylsulfinyloxy, arylsulfonyloxy, arylsulfinyloxy, aryloxy, aralkoxy or heterocyclooxy.

14. Synthesis intermediates selected from the group consisting of 3-ethynyl-1-azabicyclo[2.2.2]oct-3-yl acetate, (3R)-3-ethynyl-1-azabicyclo[2.2.2]oct-3-yl acetate, (3R)-3-ethynyl-1-azabicyclo[2.2.2]octan-3-ol compound complexed with borane (1:1), (3R)-3-ethynyl-3-methoxy-1-azabicyclo[2.2.2]octane with borane, (3R)-3-ethynyl-1-azabicyclo[2.2.2]oct-3-yl methyl ether, (3R)-3-ethoxy-3-ethynyl-1-azabicyclo[2.2.2]octane, (3R)-3-(benzyloxy)-3-ethynyl-1-azabicyclo[2.2.2]octane, (3R)-3-ethynyl-3-[(3-methylbenzyl)oxy]-1-azabicyclo[2.2.2]octane, 3-ethynyl-3-fluoroquinuclidine, 3-[(3R)-3-methoxy-1-azabicyclo[2.2.2]oct-3-yl]-1-phenyl-1-(3-pyridinyl)-2-propynyl acetate, 3-[(3R)-3-methoxy-1-azabicyclo[2.2.2]oct-3-yl]-1,1-di(2-thienyl)-2-propyn-1-ol compound complexed with borane (1:1), methyl {[3-[(3R)-3-methoxy-1-azabicyclo[2.2.2]oct-3-yl]-1,1-di(2-thienyl)-2-propynyl]oxy}acetate compound complexed with borane (1:1), 3-(3,3-diphenyl-1-butynyl)quinuclidin-3-ol, 3-(3,3-diphenyl-1-butynyl)quinuclidin-3-ol complexed with borane (1:1), 3-(3,3-diphenyl-1-butynyl)-1-azabicyclo[2.2.2]oct-3-yl methyl ether compound complexed with borane (1:1), 4-(3-hydroxy-1-azabicyclo[2.2.2]oct-3-yl)-2,2-diphenyl-3-butynenitrile, 4-(3-hydroxy-1-azabicyclo[2.2.2]oct-3-yl)-2,2-diphenyl-3-butynenitrile complexed with borane (1:1), 4-(3-methoxy-1-azabicyclo[2.2.2]oct-3-yl)-2,2-diphenyl-3-butynenitrile compound complexed with borane (1:1), 3-[(3R)-3-methoxy-1-azabicyclo[2.2.2]oct-3-yl]-1,1-diphenyl-2-propyn-1-ol compound complexed with borane (1:1), (3R)-3-methoxy-3-(3-methoxy-3,3-diphenyl-1-propynyl)-1-azabicyclo[2.2.2]octane compound complexed with borane (1:1) and 3-cycloheptyl-1-[(3R)-3-methoxy-1-azabicyclo[2.2.2]oct-3-yl]-5-(trimethylsilyl)-1.

* * * * *